US006625856B2

(12) United States Patent
Tezuka

(10) Patent No.: US 6,625,856 B2
(45) Date of Patent: Sep. 30, 2003

(54) METHOD OF MANUFACTURING AN ULTRASONIC TRANSDUCER

(75) Inventor: Satoru Tezuka, Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 218 days.

(21) Appl. No.: 09/911,467

(22) Filed: Jul. 25, 2001

(65) Prior Publication Data

US 2001/0044995 A1 Nov. 29, 2001

Related U.S. Application Data

(62) Division of application No. 09/456,402, filed on Dec. 8, 1999, now Pat. No. 6,308,389.

(30) Foreign Application Priority Data

Dec. 9, 1998 (JP) ............................................. 10-350193

(51) Int. Cl.$^7$ ............................................. H04R 17/00
(52) U.S. Cl. ...................... 29/25.35; 29/594; 29/603.13; 29/603.14; 29/603.16; 29/609.1; 29/759; 264/263; 264/272.14; 264/272.16
(58) Field of Search ............................... 29/25.35, 594, 29/603.13, 603.14, 603.16, 609.1, 759, 883; 264/263, 272.14, 272.16

(56) References Cited

U.S. PATENT DOCUMENTS

| | | | | |
|---|---|---|---|---|
| 4,217,684 A | * | 8/1980 | Brisken et al. ............. | 29/25.35 |
| 4,611,372 A | * | 9/1986 | Enjoji et al. ................ | 29/25.35 |
| 4,747,192 A | | 5/1988 | Rokurota ................... | 29/25.35 |
| 4,825,115 A | * | 4/1989 | Kawabe et al. ............. | 310/327 |
| 4,939,826 A | * | 7/1990 | Shoup ........................ | 29/25.35 |
| 5,044,053 A | * | 9/1991 | Kopel et al. ................ | 29/25.35 |
| 5,267,221 A | | 11/1993 | Miller David G. et al. . | 367/140 |
| 5,311,095 A | | 5/1994 | Smith et al. ................ | 29/25.35 |
| 5,329,498 A | | 7/1994 | Greenstein .................. | 367/155 |
| 5,457,863 A | | 10/1995 | Thomas, III et al. ...... | 29/25.35 |
| 5,559,388 A | | 9/1996 | Lorraine et al. ............ | 310/334 |
| 5,592,730 A | | 1/1997 | Greenstein et al. .......... | 29/594 |
| 5,644,085 A | | 7/1997 | Lorraine et al. ............. | 73/641 |
| 5,711,058 A | * | 1/1998 | Frey ........................... | 29/25.35 |
| 6,038,752 A | * | 3/2000 | Finsterwald et al. ....... | 29/25.35 |
| 6,110,314 A | * | 8/2000 | Nix et al. ................... | 156/218 |

OTHER PUBLICATIONS

Stephen W. Smith, et al. "Update on 2–D Array Transducers for Medical Ultrasound", 1995 IEEE Ultrasonics Symposium, pp. 1273–1278, Jun. 1995.

J–M Bureau, et al. "A Two–Dimensional Transducer Array For Real–Time 3D Medical Ultrasound Imaging", 1998 IEEE Ultrasonic Symposium, 4 pages.

Larry Daane, et al. "A Demountable Interconnect System for a 50×50 Ultrasonic Imaging Transducer Array", IEEE Transactions on Ultrasonics, Ferroelectrics, and Frequency Control, vol. 44, No. 5, pp. 978–982, Sep. 1997.

E. D. Light, et al. "Progress in Two–Dimensional Arrays for Real–Time Volumetric Imaging", Ultrasonic Imaging 20, 1998, pp. 1–15.

Richard E. Davidsen, et al. Two–Dimensional Arrays for Medical Ultrasound Using Multilayer Flexible Circuit Interconnection, IEEE Transactions on Ultrasonics, Ferroelectronics, and Frequency Control, vol. 45, No. 2, pp. 338–348, Mar. 1998.

Michael Greenstein, et al. A 2.5 MHz 2D Array with Z–Axis Electrically Conductive Backing, IEEE Transactions on Ultrasonic, Ferroelectronics, and Frequency Control, vol. 44, No. 5, pp. 970–977, Sep. 1977.

* cited by examiner

Primary Examiner—A. Dexter Tugbang
Assistant Examiner—Paul D Kim
(74) Attorney, Agent, or Firm—Oblon, Spivak, McClelland, Maier & Neustadt, P.C.

(57) ABSTRACT

This invention relates to a method of manufacturing an ultrasonic transducer. A plurality of leads end portions are inserted into a plurality of lead holes of an alignment jig. A backing layer is formed by resin molding. After that, the alignment jig is removed from the surface of the backing layer, and the surface of the backing layer is flattened. Since the end portions of the leads are exposed to this flattened surface of the backing layer, discrete electrodes formed on the back surfaces of transducer elements are electrically connected to these lead end portions. The accuracy of lead arrangement is thus improved by the use of the alignment jig. This reduces alignment errors of leads with respect to the discrete electrodes of the transducer elements.

18 Claims, 17 Drawing Sheets

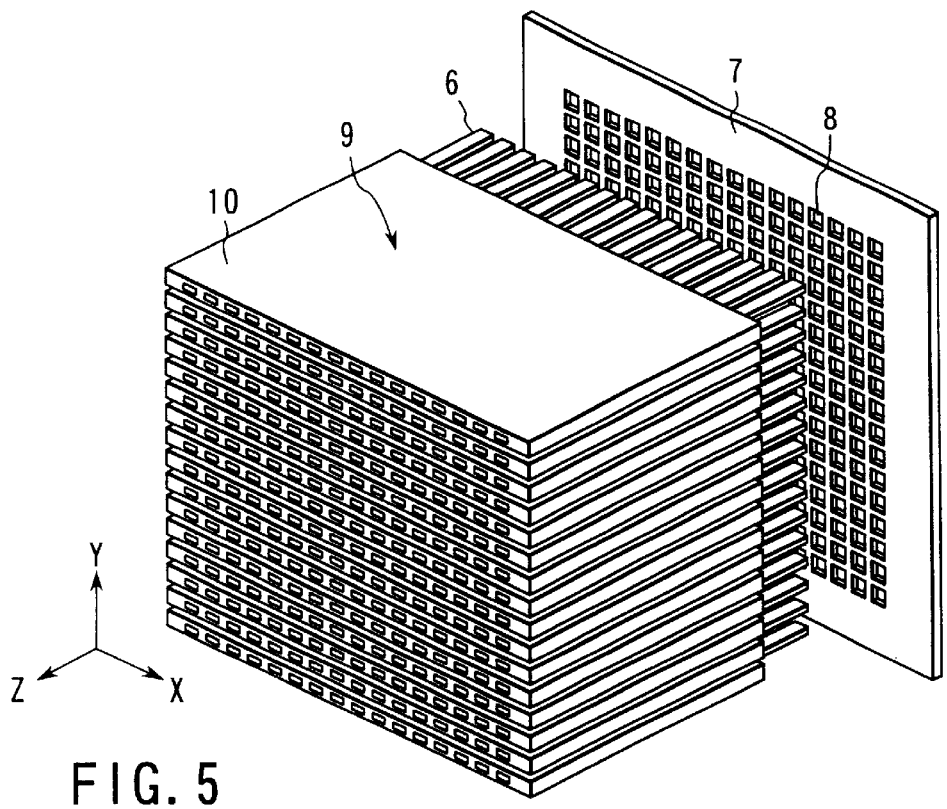
FIG. 5
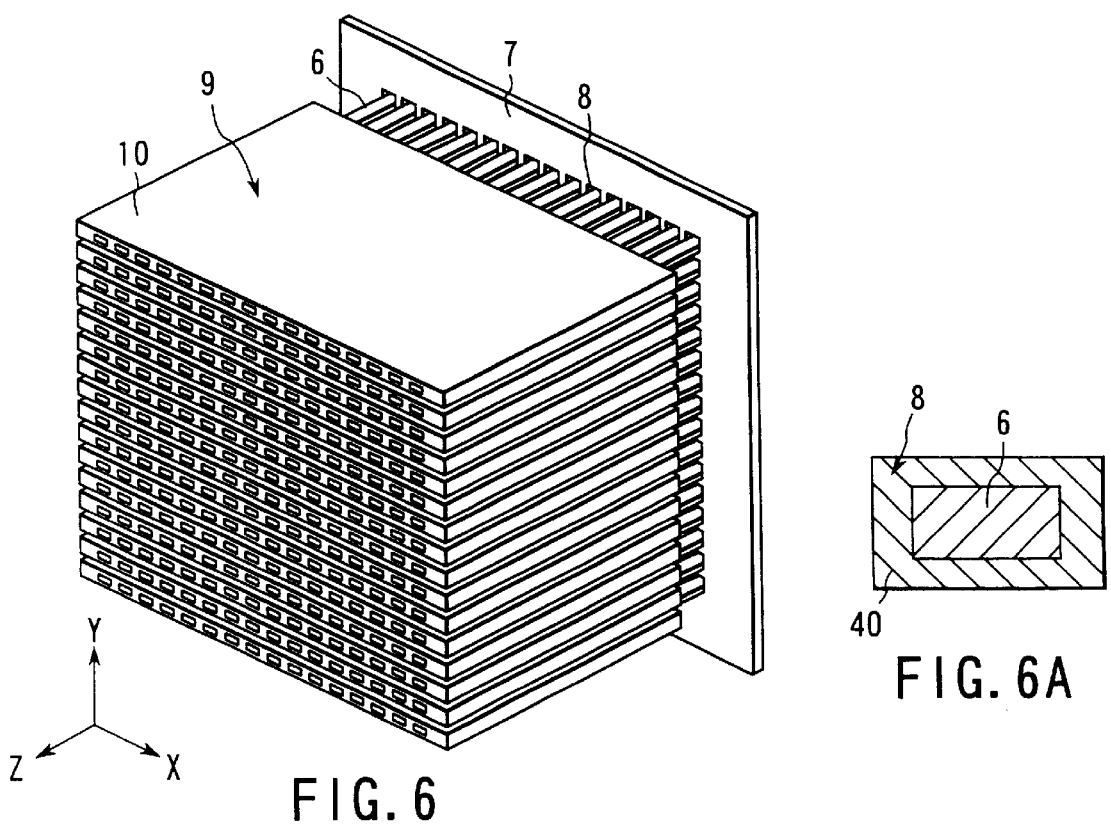
FIG. 6
FIG. 6A

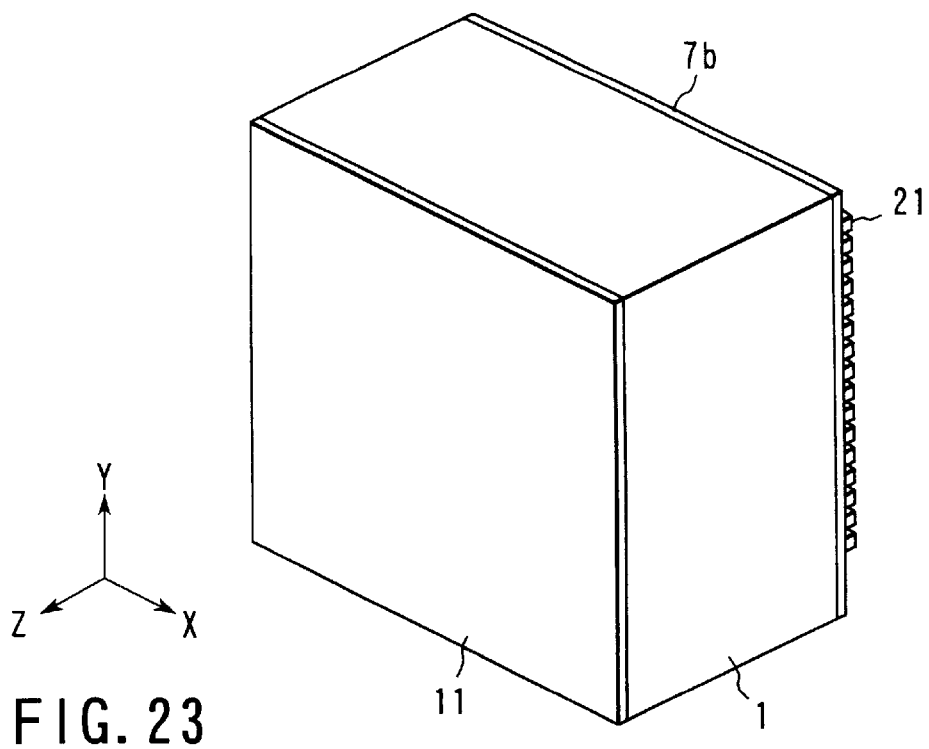
F I G. 23
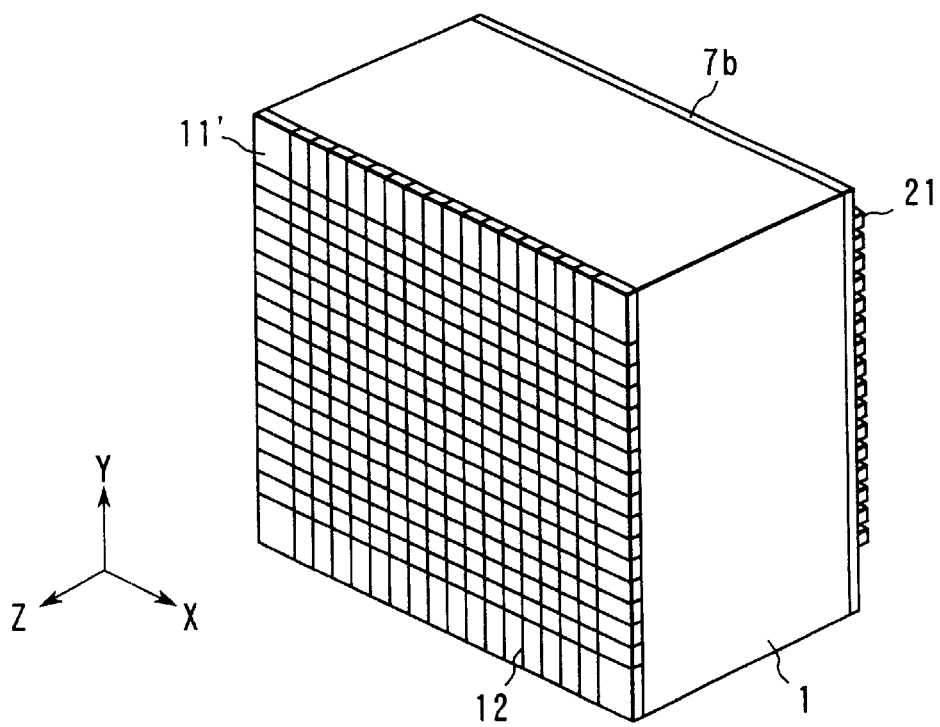
F I G. 24

METHOD OF MANUFACTURING AN ULTRASONIC TRANSDUCER

The present document is a divisional of Parent U.S. application Ser. No. 09/456,402 now U.S. Pat. No. 6,308,389, filed Dec. 8, 1999 which in turn is based on Japanese Priority Document 10-350,193, filed in the Japanese Patent Office on Dec. 9, 1998, the entire contents of each of which documents are incorporated herein by reference.

BACKGROUND OF THE INVENTION

The present invention relates to an ultrasonic transducer as a main component of an ultrasonic probe of an ultrasonic apparatus such as an ultrasonic diagnostic apparatus and a method of manufacturing the same and, more particularly, to a two-dimensional array type ultrasonic transducer in which transducer elements for reversibly converting an electrical signal and an ultrasonic signal are arrayed in a matrix (two-dimensionally) and a method of manufacturing the same.

Various apparatuses using ultrasonic waves are widely used in the field of medicine. Of these apparatuses using ultrasonic waves, the most extensively used is an ultrasonic diagnostic apparatus which obtains tomographic images of soft tissues of living bodies by using the ultrasonic pulse reflection method. This ultrasonic diagnostic apparatus is known as a noninvasive method and displays a tomographic image of a tissue. Compared to other diagnostic apparatuses such as an X-ray diagnostic apparatus, an X-ray computer tomographic apparatus, a magnetic resonance imaging apparatus, and a nuclear medicine diagnostic apparatus, an ultrasonic diagnostic apparatus has the advantages that it can display images in real time, is small and inexpensive, has high safety with no exposure to X-rays, and is capable of blood flow imaging by using the ultrasonic Doppler method.

For these reasons, ultrasonic diagnostic apparatuses are extensively used in examinations of hearts, abdomens, mammary glands, and urinary organs, and in obstetrics and gynecology. Also, an ultrasonic diagnostic apparatus can display, e.g., heart beats and the motions of an unborn child in real time with a simple operation of bringing an ultrasonic probe into contact with the body surface, and can allow repetitive examinations because of its high safety. Additionally, examinations can be readily performed even on the bedside.

To generate a tomographic image of the interior of an object to be examined, an ultrasonic diagnostic apparatus scans an internal section of the object via an ultrasonic probe. This scan is classified into two types in accordance with the principle of scanning: one is mechanical scan by which an ultrasonic transducer is mechanically moved, and the other is electronic scan which uses electronic switching and delay control of arrayed transducer elements. The scan is also classified into two other types in accordance with the range of scanning: one is two-dimensional scan which scans a section with an ultrasonic beam, and the other is three-dimensional scan which scans an internal three-dimensional region of an object with an ultrasonic beam. The currently most frequently used three-dimensional scan is to translate or axially rotate, a two-dimensional scan type ultrasonic probe either manually or mechanically.

Since this three-dimensional scan requires a long scanning time, the time resolution of the scan is low, so the scan is impractical. To improve the time resolution, it is essential to use a two-dimensional array type ultrasonic probe in which a plurality of transducer elements are arrayed in a matrix and to scan a three-dimensional region electronically by using electronic switching and delay control of these transducer elements.

In the manufacture of a two-dimensional array type ultrasonic transducer to be incorporated into this two-dimensional array type ultrasonic probe, one of the most difficult problems to solve is a method of extracting leads from transducer elements arrayed at fine pitches.

One example is a method by which a conductor pad array formed in a matrix on the surface of a printed board is adhered to a discrete electrode array of transducer elements. Methods of electrically connecting the conductor pads on a printed board to the discrete electrodes of the transducer elements are: (1) a method using a conductive adhesive; (2) a method of heating, under pressure, an anisotropic conductive film sandwiched between the conductor pad array and the discrete electrode array of the transducer elements; and (3) a method of contact-bonding metal bumps formed on the conductor pads and on the discrete electrodes.

Unfortunately, in the method (1) the interval between the transducer elements must be increased in order to avoid conduction between adjacent discrete electrodes. Also, the methods (2) and (3) have the problems of, e.g., breakage of the transducer elements, depolarization (polarization shift) of the transducer elements heated in the connecting operation, and thermal deformation of the printed board, since these methods require pressing and/or heating. Further, these methods (1) to (3) have the common problem that the acoustic characteristics (wavelength, frequency band) of the ultrasonic transducer itself degradate in accordance with the acoustic characteristics of the printed board directly adhered to the transducer elements.

Furthermore, in the case the transducer plate is divided to obtain the transducer element array after the transducer plate is sticked on the printed circuit board, wiring on the printed circuit board are breaked. Therefore the element array after is defective in division.

To solve these problems, a method of burying a plurality of leads in a backing layer is being studied. In this method, elements certainly are separated to each other by gaps attained to the backing layer. However, the yield is low because the alignment of the leads with the discrete electrodes is not easy.

BRIEF SUMMARY OF THE INVENTION

It is an object of the present invention to reduce alignment errors of leads with respect to discrete electrodes of transducer elements in a two-dimensional array type ultrasonic transducer and in a method of manufacturing the same.

The present invention relates to a method of manufacturing an ultrasonic transducer. First, a plurality of printed boards in each of which a plurality of leads are formed in a line are stacked. The end portions of the leads protrude from each printed board. These lead end portions are inserted into a plurality of lead holes or lead slits of an alignment jig. The plurality of printed boards are buried in the back surface of this alignment jig, and a backing layer is formed by resin molding. After that, the alignment jig is removed from the surface of the backing layer, and the surface of the backing layer is flattened. Since the end portions of the leads are exposed to this flattened surface of the backing layer, discrete electrodes formed on the back surfaces of transducer elements are electrically connected to these lead end portions. The accuracy of lead arrangement is thus improved by the use of the alignment jig. Therefore, alignment errors of the leads with respect to the discrete electrodes of the transducer elements can be reduced.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5 is a view showing a step of aligning leads of flexible printed boards with the alignment jig in the method of manufacturing the ultrasonic transducer according to the first embodiment;

FIG. 6 is a view showing a step of inserting the leads of the flexible printed boards into lead holes of the alignment jig in the method of manufacturing the ultrasonic transducer according to the first embodiment;

FIG. 6A is a plan view showing the lead fixed to the alignment jig by a conductive adhesive;

FIG. 23 is a view showing a step of forming a thin metal film on the surface of the backing layer in the method of manufacturing the ultrasonic transducer according to the second embodiment;

FIG. 24 is a perspective view showing a step of separating the thin metal film in the method of manufacturing the ultrasonic transducer according to the second embodiment;

DETAILED DESCRIPTION OF THE INVENTION

Practical embodiments of an ultrasonic transducer and a method of manufacturing the same according to the present invention will be described in detail below with reference to the accompanying drawings. Note that an ultrasonic transducer is a main component for transmitting and receiving ultrasonic waves in an ultrasonic probe of an ultrasonic diagnostic apparatus.

First Embodiment

Figure 1:
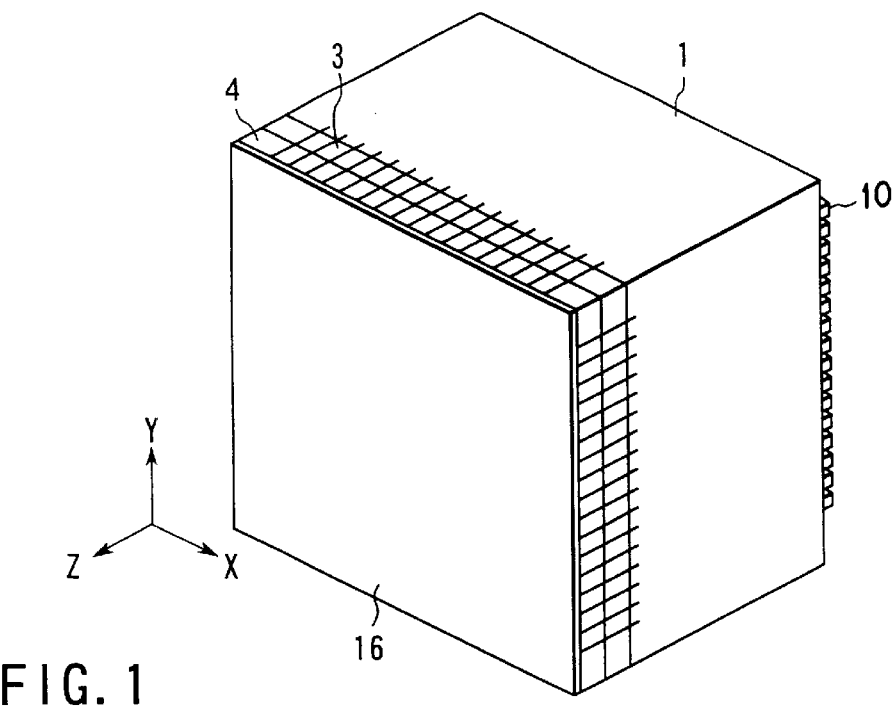
FIG. 1 is a perspective view of an ultrasonic transducer according to the first embodiment of the present invention.
Figure 2:
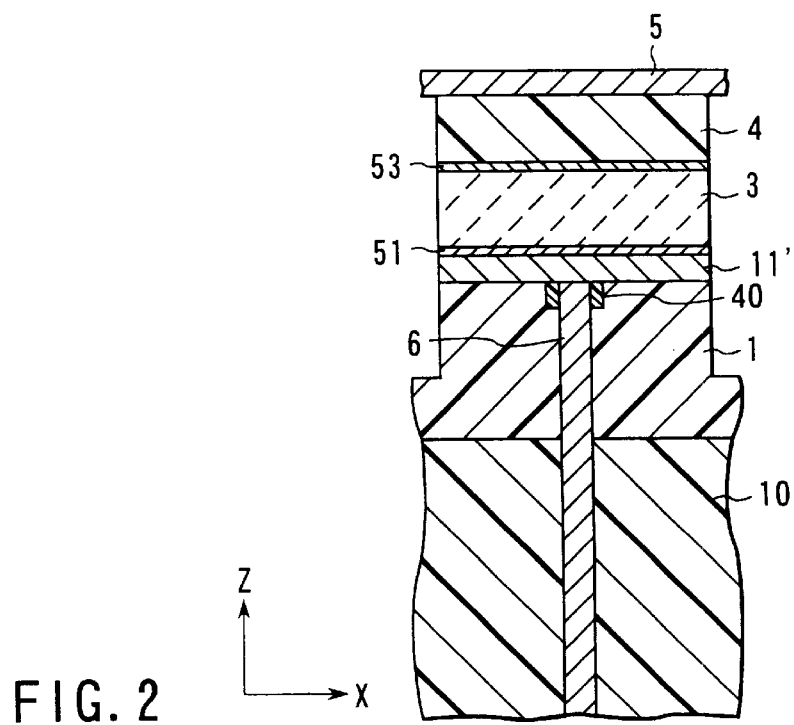
FIG. 2 is an X-Z sectional view of one element of the ultrasonic transducer shown in FIG. 1.

As shown in FIGS. 1 and 2, an ultrasonic transducer according to the first embodiment has a backing layer 1 for damping ultrasonic waves. Stacked flexible printed boards 10 are buried in this backing layer 1. Leads 6 are formed in a line in each printed board 10. Note that these leads 6 are buried in the substrate material 9, or formed on the substrate material 9 and covered with an insulating layer. Electronic circuits such as amplifier circuits may be formed on each printed board 10.

The front ends of the leads 6 are exposed to the front surface of the backing layer 1 and fixed by conductive resins 40. The rear ends of the leads 6 protrude from the back surface of the backing layer 1. Transducer elements 3 are arrayed in a matrix on the front surface of the backing layer 1. Discrete electrodes 51 are formed on the back surfaces of the transducer elements 3. Common electrodes 53 for grounding are formed on the front surfaces of the transducer elements 3. The front ends of the leads 6 are electrically connected to the discrete electrodes 51 via contacts 11'. Acoustic matching layers 4 having conductivity are mounted on the transducer elements 3. A conductive film 16 for grounding is formed on these acoustic matching layers 4.

A method of manufacturing the ultrasonic transducer according to this embodiment will be described below.

Figure 3A:
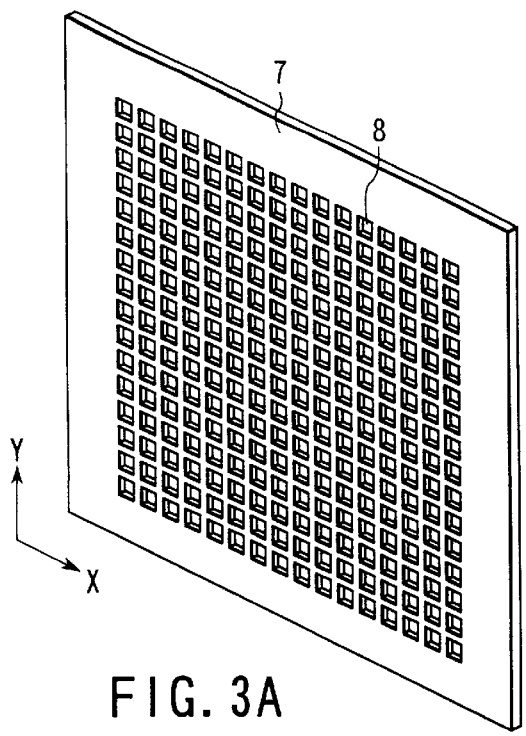
FIG. 3A is a perspective view of an alignment jig used in a method of manufacturing the ultrasonic transducer according to the first embodiment.
Figure 3B:
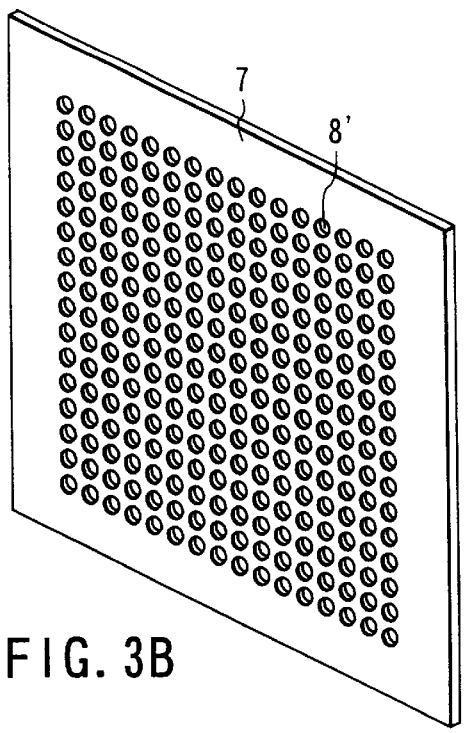
FIG. 3B is a perspective view of another alignment jig.

FIG. 3A shows a plate-like alignment jig 7 for aligning the leads 6 with the discrete electrodes 51 of the transducer elements 3. Lead holes 8 are formed in a matrix in this alignment jig 7 in accordance with the arrangement of the transducer elements 3. These lead holes 8 are formed to be slightly larger than the diameter of the leads 6 so as to allow insertion of the leads 6. The lead holes 8 need not be substantially rectangular holes as shown in FIG. 3A but can be circular lead holes 8' as shown in FIG. 3B. This alignment jig 7 is manufactured by forming lead holes 8, by mechanical processing such as drilling, laser processing, or etching processing, in a plate made of a material, such as ceramics, metal, or resin, which allows easy drilling. That is, the alignment jig 7 is made of a material, such as ceramics, metal, or resin, which is easy to process, and holes are formed by mechanical processing such as drilling, laser processing, or etching processing, each having high processing accuracy. Consequently, the lead holes 8 can be arranged with high accuracy.

The alignment jig need not be a single member, but may have a multilayered structure made of workable materials such as a ceramic, metal, and resin. The lead hole formed in the alignment jig need not be a through hole extending through the alignment jig, but may be a blind groove formed midway along the thickness of the alignment jig.

Figure 4:
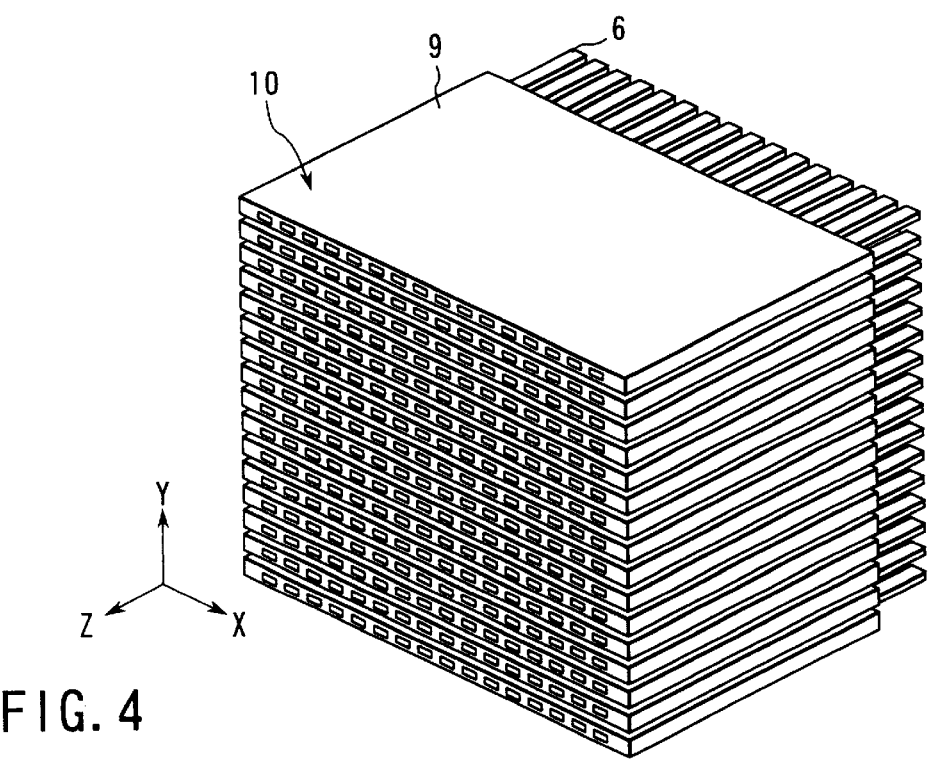
FIG. 4 is a view showing a flexible printed board stacking step in the method of manufacturing the ultrasonic transducer according to the first embodiment.

First, as shown in FIG. 4, the printed boards 10 are stacked. In these printed boards 10, the leads 6 are buried in a line in substrate materials 9. The end portions of these leads 6 protrude, into the form of a comb, from the printed boards 10. The printed boards 10 are so stacked that the leads 6 are arranged in a matrix.

Next, as shown in FIGS. 5 and 6, the end portions of the leads 6 are inserted into the lead holes 8 of the alignment jig 7. Since the lead holes 8 are arranged in accordance with the arrangement of the transducer elements 3, the leads 6 are also arranged in accordance with the arrangement of the transducer elements 3. As shown in FIG. 6A, the gaps between the lead holes 8 and the leads 6 are filled with the conductive resins 40. Consequently, the printed boards 10 are fixed to the alignment jig 7. Note that the material to be charged into the lead holes 8 need not be a conductive resin and can be an insulating resin.

In the above step, the leads 6 of one printed board 10 are inserted into one line of the lead holes 8. However, the leads 6 of a plurality of printed boards 10 can also be inserted into one line of the lead holes 8. Also, in the above structure the leads 6 are formed in a line in one printed board 10. However, the leads 6 can also be formed in a plurality of lines in one printed board 10.

Figure 7:
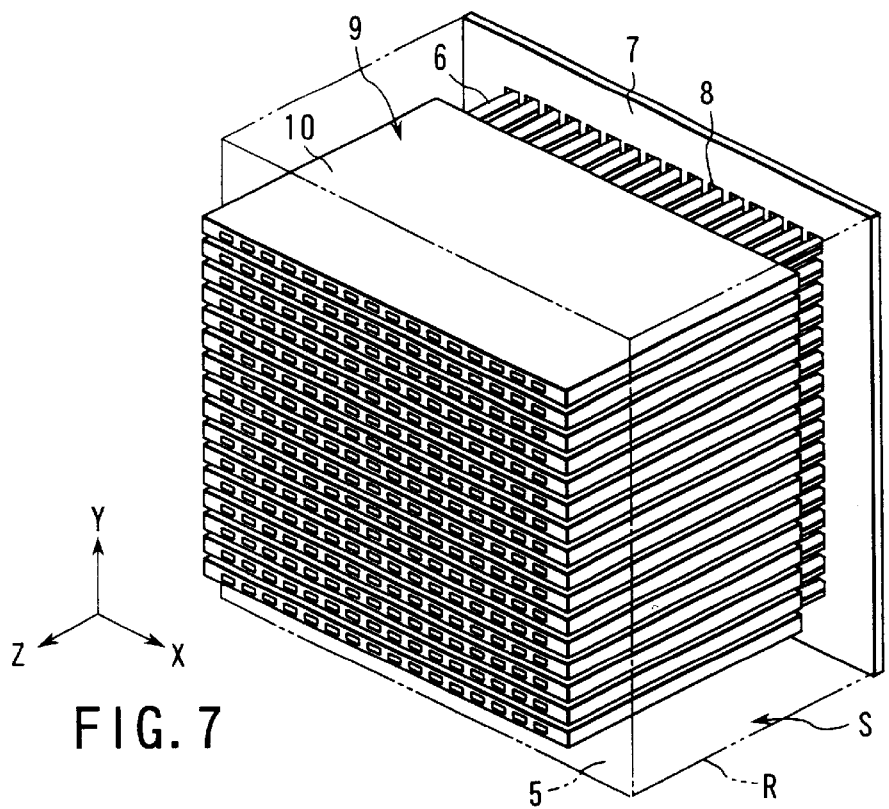
FIG. 7 is a perspective view showing a molding region R of a backing resin S in the method of manufacturing the ultrasonic transducer according to the first embodiment.
Figure 8:
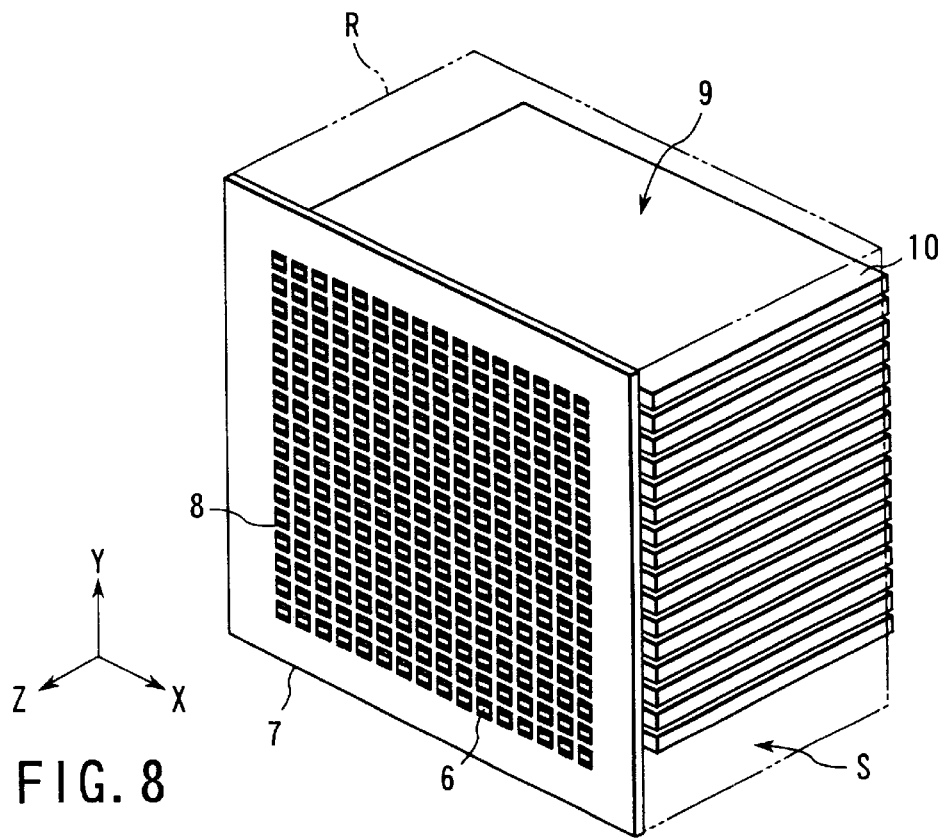
FIG. 8 is a perspective view showing the molding region R of the backing resin S viewed in a different direction from that in FIG. 7.

As shown in FIGS. 7 and 8, a relatively soft resin S for backing having high ultrasonic damping performance is formed by molding in a rectangular parallelepiped region R on the back surface of the alignment jig 7 including the stacked printed boards 10. As a consequence, the printed boards 10 are buried in the resin S. As this resin S, a material having appropriate acoustic impedance and appropriate acoustic attenuation by which it functions as an acoustic damper is chosen. The resin S changes into the backing layer 1 by hardening.

Another method of forming the backing layer is to insert a resin sheet in a gap between printed boards and then inject a resin in the gap.

Figure 9:
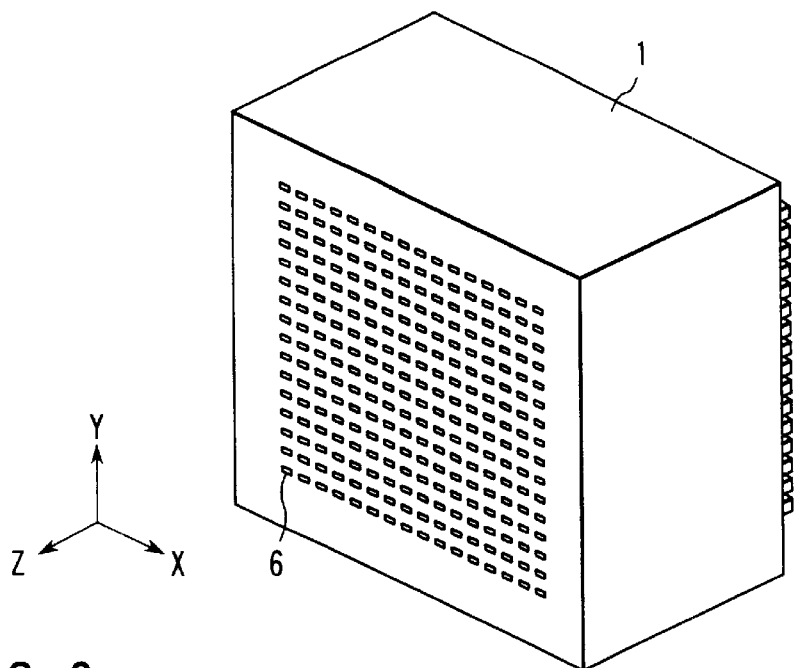
FIG. 9 is a view showing a step of removing the alignment jig from a backing layer in the method of manufacturing the ultrasonic transducer according to the first embodiment.

As shown in FIG. 9, the alignment jig 7 is removed from the surface of the backing layer 1 by, e.g., mechanical processing or etching. After that, the surface of the alignment jig 7 is flattened by cutting it together with the leads 6. This exposes the ends of the leads 6 to the surface of the backing layer 1. The alignment jig 7 can deteriorate the acoustic characteristics (e.g., the wavelength and frequency band) of the transducer elements 3. This method can avoid this inconvenience by the removal of the alignment jig 7.

Figure 10:
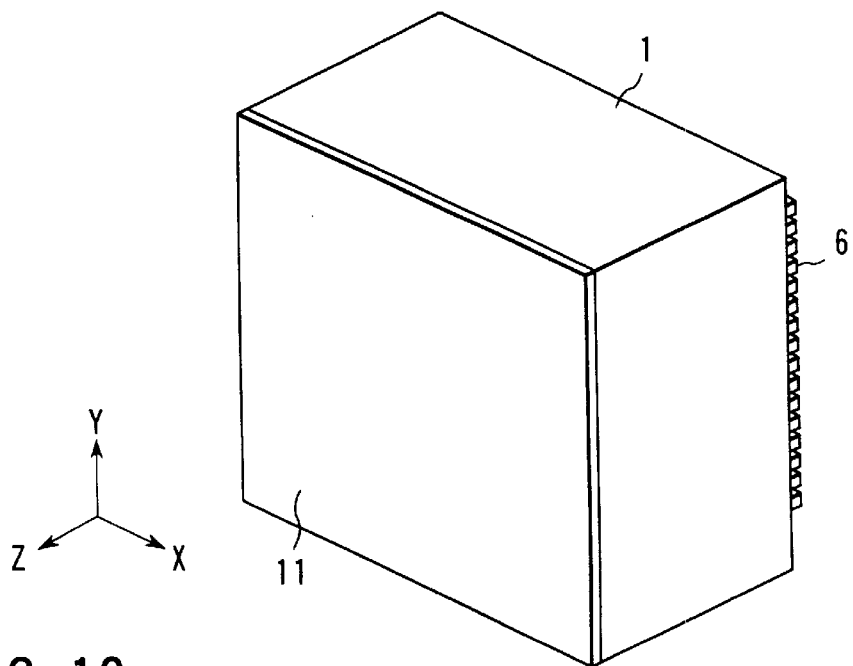
FIG. 10 is a view showing a step of forming a thin metal film on the surface of the backing layer in the method of manufacturing the ultrasonic transducer according to the first embodiment.

As shown in FIG. 10, a contact layer 11 as a thin metal film is formed on the flattened surface of the backing layer 1 by a technique such as vapor deposition or sputtering. The function of this contact layer 11 is to increase the contact area between the leads 6 and the discrete electrodes of the transducer elements 3 and thereby improve the reliability of the electrical connection between the leads 6 and the discrete electrodes of the transducer elements 3. More specifically, the contact layer 11 is a stacked structure of chromium and gold. A conductive resin may be formed thin by a technique such as printing. The thickness of this contact layer 11 is much shorter than the wavelength of ultrasonic waves generated by the transducer elements 3. So, the contact layer 11 does not change the acoustic characteristics.

Figure 11:
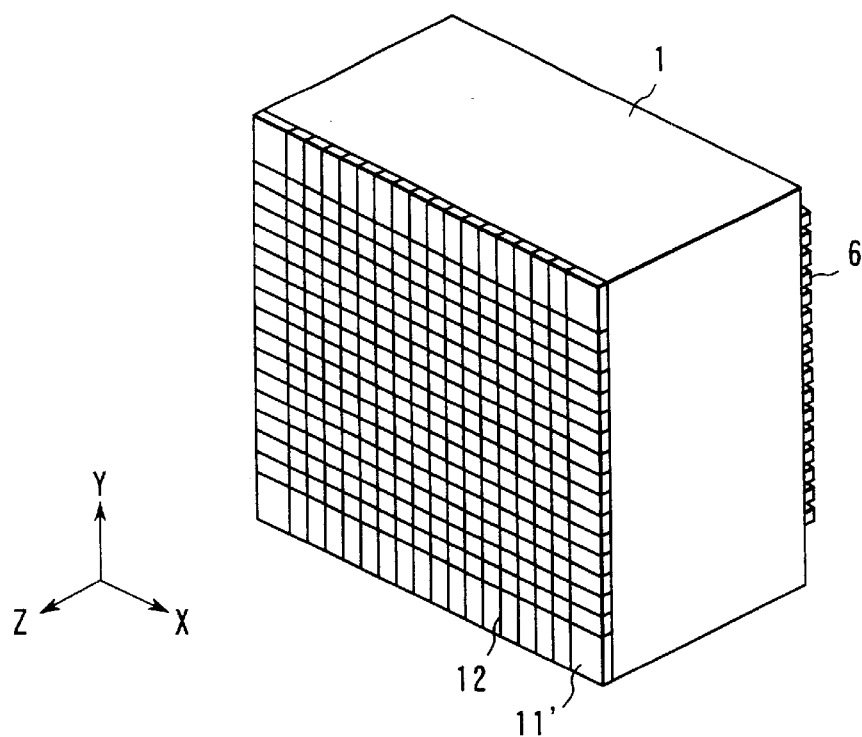
FIG. 11 is a perspective view showing a step of separating the thin metal film in the method of manufacturing the ultrasonic transducer according to the first embodiment.

As shown in FIG. 11, the contact layer 11 is separated by grooves 12 in accordance with the arrangement of the leads 6, thereby forming the contacts 11' isolated from each other.

Figure 12:
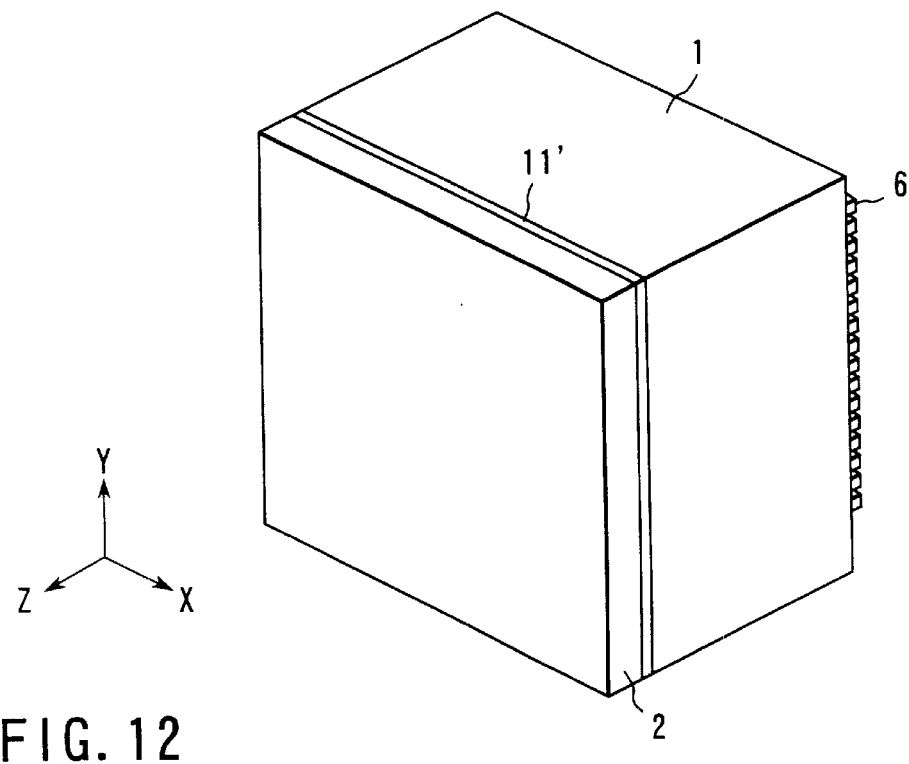
FIG. 12 is a perspective view showing a step of adhering a piezoelectric plate to the surface of the thin metal film in the method of manufacturing the ultrasonic transducer according to the first embodiment.

Next, as shown in FIG. 12, a piezoelectric plate 2 such as piezoelectric ceramics is adhered by a conductive adhesive onto the contacts 11' on the surface of the backing layer 1. A thin metal film is formed on each of the front and back surfaces of this piezoelectric plate 2. A baked silver electrode is a typical example of this thin metal film. However, some other material or some other method is also usable.

Figure 13:
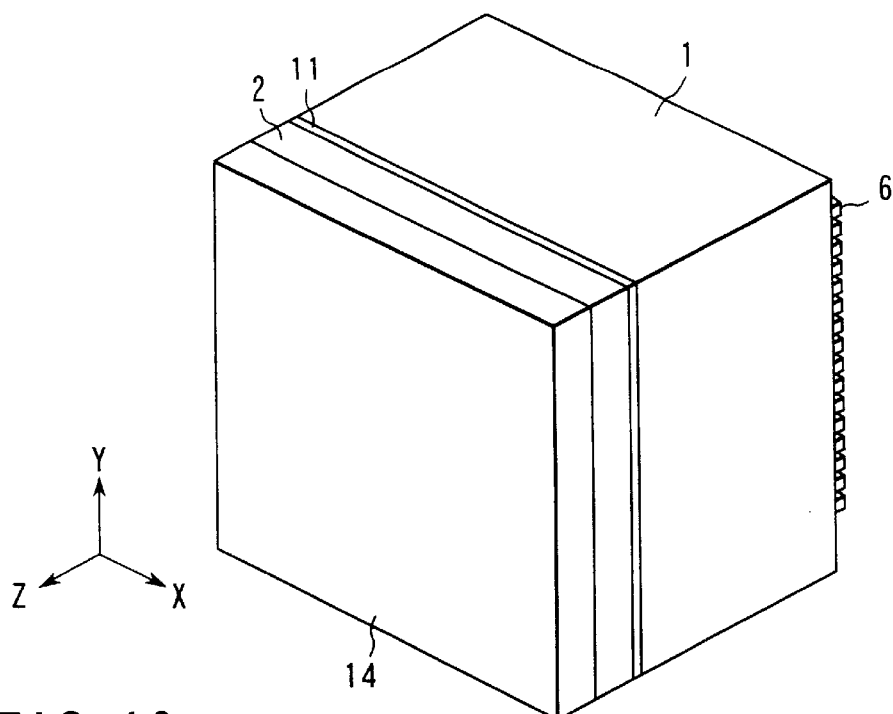
FIG. 13 is a perspective view showing a step of forming a conductive resin layer on the surface of the piezoelectric plate in the method of manufacturing the ultrasonic transducer according to the first embodiment.

As shown in FIG. 13, an acoustic matching layer 14 made of a conductive resin having a predetermined acoustic impedance is formed to have a predetermined thickness on the surface of the piezoelectric plate 2. This conductive resin is, e.g., an epoxy resin filled with a silver frit. Since this acoustic matching layer 14 has conductivity, it is electrically connected to the thin metal film on the front surface of the piezoelectric plate 2.

Figure 14:
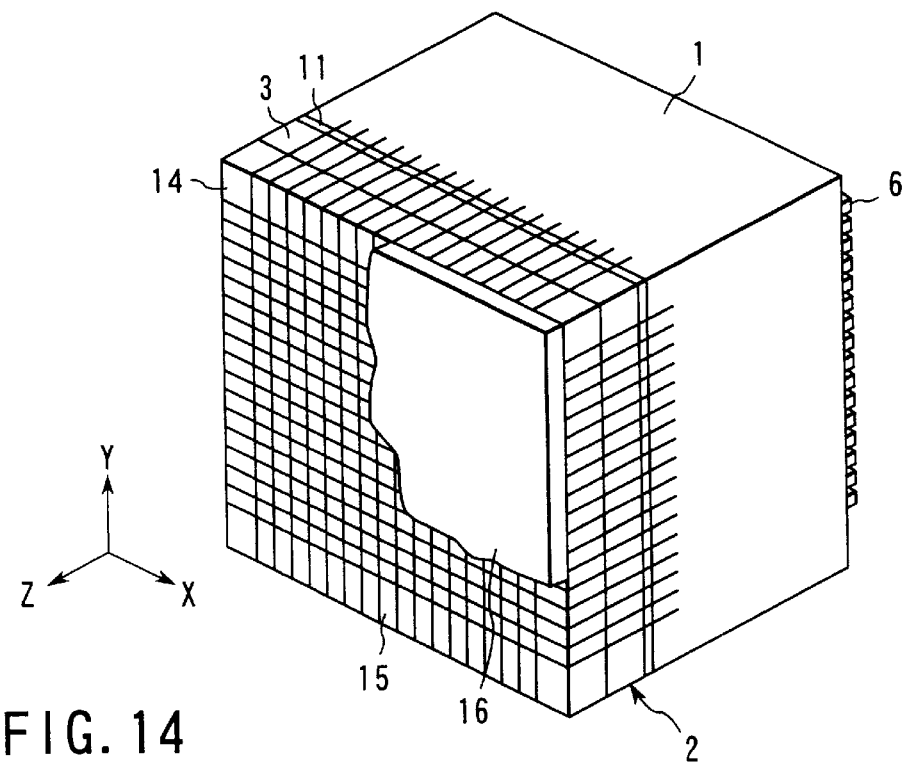
FIG. 14 is a perspective view showing a step of separating the piezoelectric plate in the method of manufacturing the ultrasonic transducer according to the first embodiment.

As shown in FIG. 14, grooves 15 are formed crosswise to extend from the surface of the acoustic matching layer 14 to the outermost portion of the backing layer 1 through the piezoelectric plate 2 in accordance with the arrangement of the leads 6. With these grooves 15, the transducer elements 3 are arrayed in a matrix. Therefore elements electrically are separated to each other.

Subsequently, the surfaces of the acoustic matching layers 14 are covered with a conductive film 16 formed by stacking a thin metal film and a resin. This conductive film 16 is, for example, formed by laminating thin-film silver on the surface of a polyethylene film. The conductive film 16 is connected to the common electrodes 53 of the transducer elements 3 via the acoustic matching layers 14. The transducer elements 3 can be grounded from this resin film 16. In this embodiment, conductive film 16 may be single layer film (e.g. metal foil).

Through the above steps, the ultrasonic transducer shown in FIG. 1 is completed. As described above, in this method the leads 6 are arranged by the alignment jig 7. This increases the arrangement accuracy of the leads 6 and reduces alignment errors with respect to the arrangement of the transducer elements 3.

Also, in this method the electrodes of the piezoelectric plate 2 are electrically connected to the leads 6 via the contacts 11'. This improves the reliability of this electrical connection. Additionally, since a conductive adhesive is used in this connection. The low pressure and heat generated by this adhesive connection causes only an acoustic characteristic deterioration. Furthermore, after the backing layer 1 and the piezoelectric plate 2 are adhered to each other, the individual transducer elements 3 are separated by the grooves 15. Accordingly, even the conductive adhesive used to adhere the backing layer 1 and the piezoelectric plate 2 can also be separated by the grooves 15. In this invention, the leads 6 are expanded from elements 3, therefore elements 3 electrically can be separated to each other by grooving after connecting between leads 6 and elements 3 using conductive adhesive. Therefore, this method does not cause breakage or polarization shift of the piezoelectric plate 2. Also, the conductive resin used as an adhesive does not generate any electrical leak between adjacent transducer elements 3. This further improves the productivity of the method.

Furthermore, the backing layer 1 interposed between the transducer elements 3 and the printed boards 10 reduces the influence of the printed boards 10 on the acoustic characteristics.

In the aforementioned method, as shown in FIG. 11, the grooves 12 are formed after the thin-film electrode 11 is formed on one principal surface of the backing layer 1, thereby dividing this thin-film electrode 11 in accordance with the wiring patterns 6. However, in this embodiment the step of forming the grooves 12 is not always necessary. That is, these grooves 12 need not be formed because the thin-film electrode 11 can be divided by forming the grooves 15 after the formation of the conductive resin layer 14 serving as the acoustic matching layers 4.

The grounding circuit can also be realized by forming grounding conductor patterns in the printed board 10 between a plurality of leads arrayed as described above or can be set by forming grounding conductor layer in the printed board 10. It is possible by forming a grounding circuit like this to reduce crosstalk between the wiring patterns.

Moreover, electronic circuits such as amplifiers and correction circuits can also be formed on the printed boards 10. This reduces the number of manufacturing steps and achieves high-density packaging.

Figure 15:
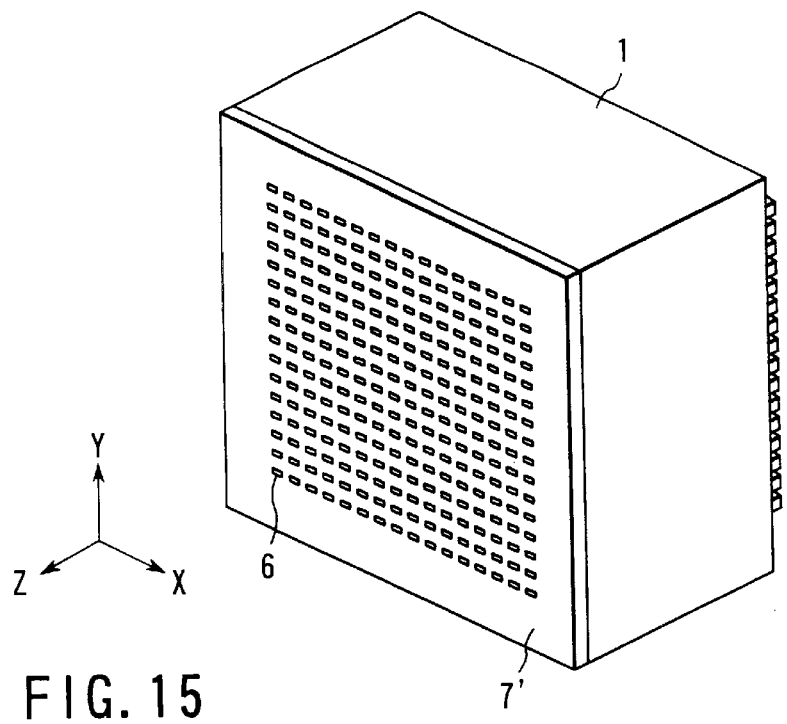
FIG. 15 is a perspective view showing a step of cutting the alignment jig, instead of removing it, in the step shown in FIG. 9.
Figure 16:
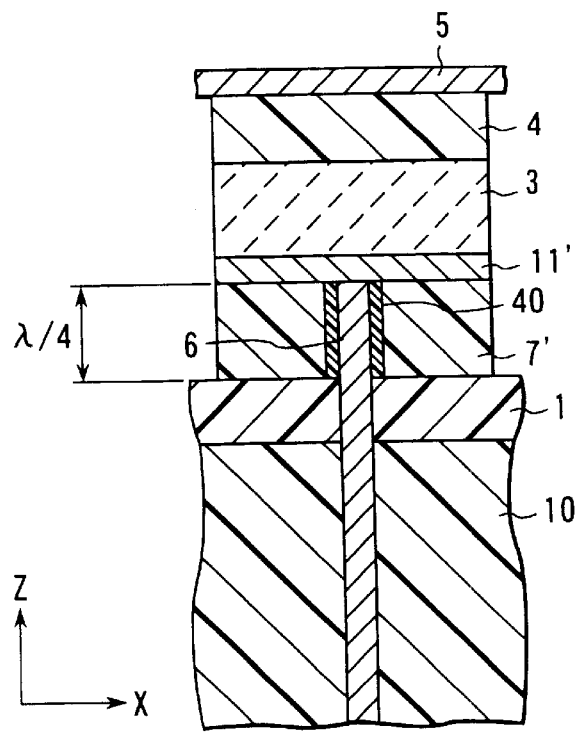
FIG. 16 is an X-Z sectional view of one transducer element of the ultrasonic transducer completed through the step shown in FIG. 15.

In the above method, in the step shown in FIG. 9 the alignment jig 7 is removed from the backing layer 1. As shown in FIGS. 15 and 16, this alignment jig 7 can also be cut, instead of being removed, to leave a thin alignment jig 7' behind. If this is the case, the thickness of this thin alignment jig 7' is substantially adjusted to be an odd integer multiple of $\lambda/4$ where $\lambda$ is the wavelength of ultrasonic waves (center frequency) generated by the transducer elements 3. Hence, the ultrasonic waves generated by the transducer elements 3 are transmitted through the alignment jig 7', without being reflected by it, and propagate to the backing layer 1. Consequently, the acoustic characteristics remain unaffected.

Second Embodiment

Figure 17:
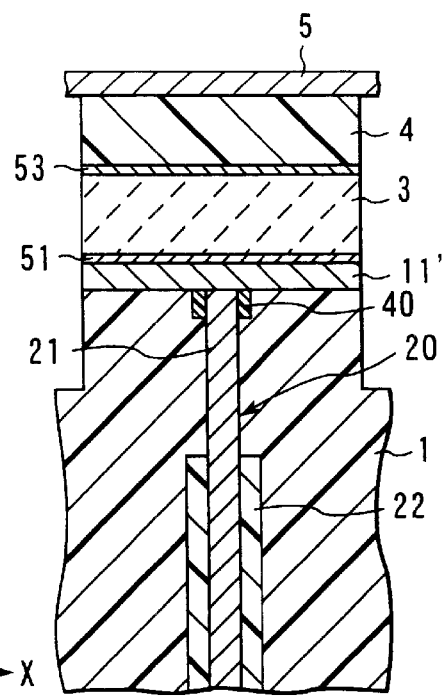
FIG. 17 is a sectional view of one transducer element of an ultrasonic transducer according to the second embodiment of the present invention.

The second embodiment of the present invention will be described below. In the explanation of this second embodiment, the same reference numerals as in the first embodiment denote the same parts, and a detailed description thereof will be omitted. In this second embodiment, as shown in FIG. 17, leads 20 are not formed in printed boards but buried in a backing layer 1, as isolated bar-like conductive wire materials. The front and rear ends of each lead 20 are exposed, and the remaining portion is covered with an insulating material 22.

Steps of manufacturing an ultrasonic transducer according to the second embodiment will be described below.

Figure 18:
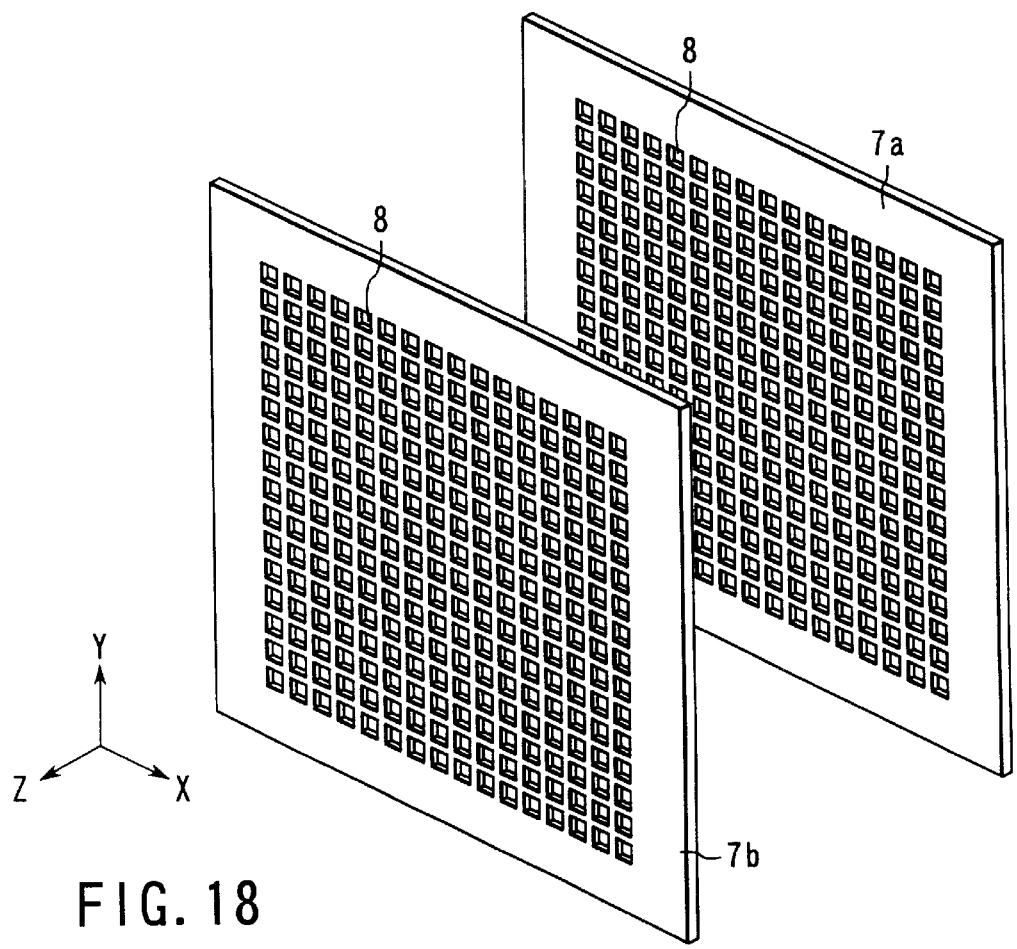
FIG. 18 is a perspective view showing a pair of alignment jigs used in a method of manufacturing the ultrasonic transducer according to the second embodiment.
Figure 19:
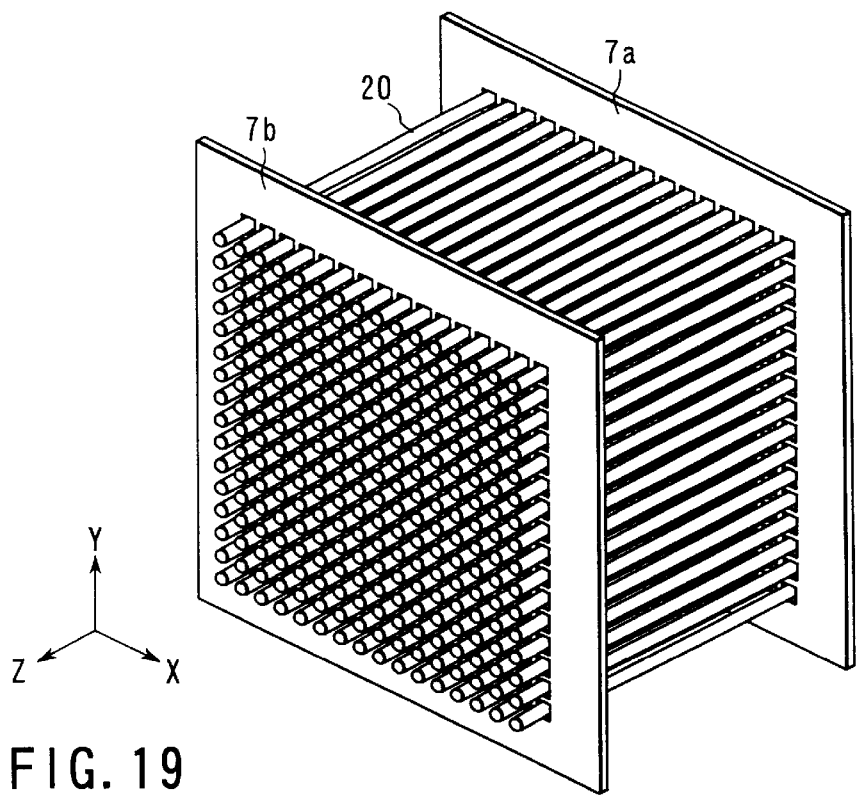
FIG. 19 is a perspective view showing a step of inserting leads into lead holes of the alignment jigs in the method of manufacturing the ultrasonic transducer according to the second embodiment.

First, as shown in FIG. 18, a pair of alignment jigs 7a and 7b having lead holes 8 formed in a matrix in accordance with the arrangement of transducer elements 3 are opposed to each other. Next, as shown in FIG. 19, the leads 20 are inserted between the lead holes 8 of the alignment jig 7a and the lead holes 8 of the alignment jig 7b. The gaps between the lead holes 8 and the leads 20 are filled with a conductive resin. The uncovered front and rear ends of the leads 20 project from the alignment jigs 7a and 7b. Therefore, adjacent ones of the leads 20 do not contact each other, and these leads 20 are accurately arranged in accordance with the arrangement of the transducer elements 3. Since the lead holes 8 of the alignment jigs 7a and 7b are accurately arranged in accordance with the arrangement of the transducer elements 3, it is readily possible to accurately arrange the leads 20 in accordance with the arrangement of the transducer elements 3. This obviates cumbersome adjustment of the arrangement of the leads 20.

Note that the leads 20 can also be arranged by a single alignment jig 7a, not by the pair of alignment jigs 7a and 7b. If this is the case, a surface formed by using the alignment jig 7a is the surface to be brought into contact with the transducer elements 3.

Figure 20:
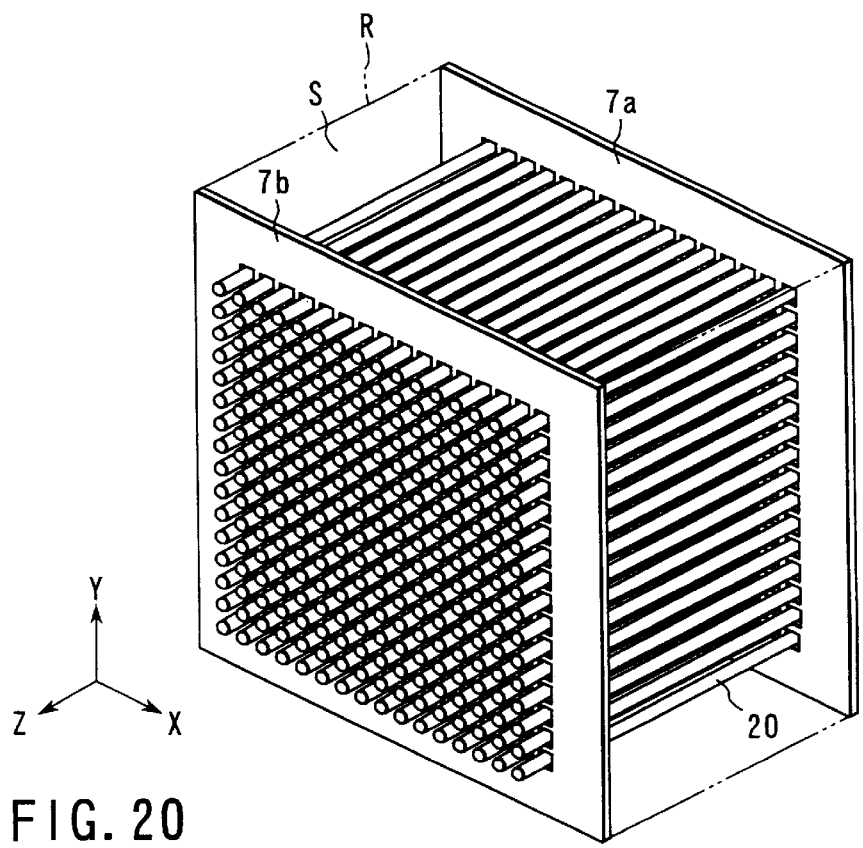
FIG. 20 is a perspective view showing a molding region R of a backing resin S in the method of manufacturing the ultrasonic transducer according to the second embodiment.
Figure 21:
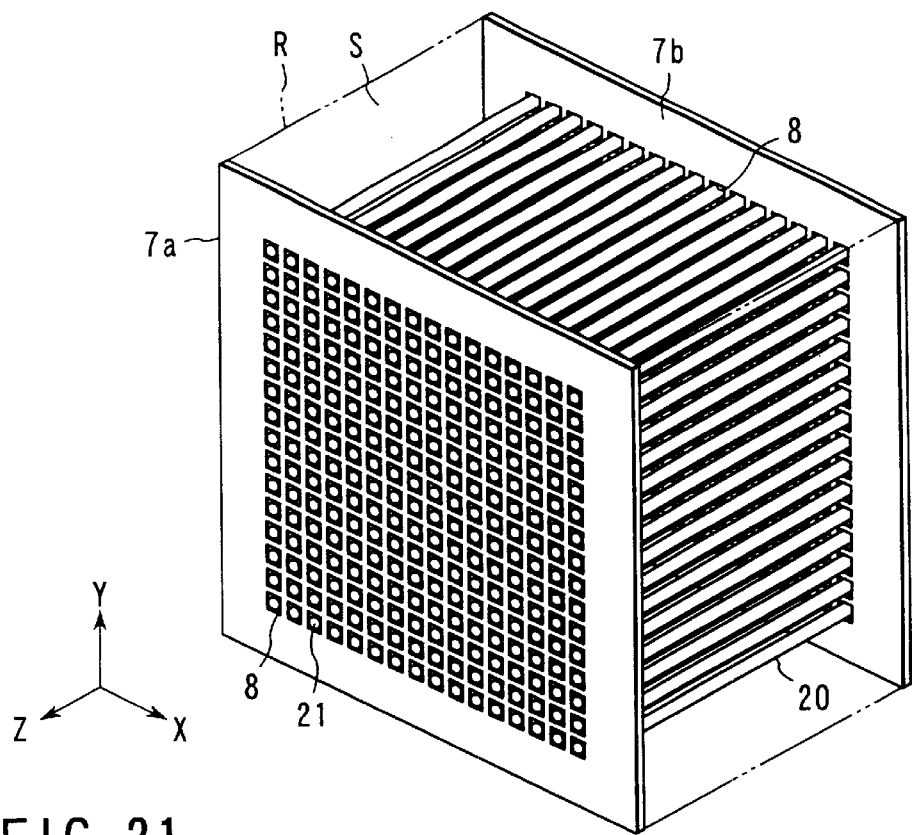
FIG. 21 is a perspective view showing the molding region R of the backing resin S viewed in a different direction from that in FIG. 20.

Next, as shown in FIGS. 20 and 21, a backing resin S is formed by molding in a rectangular parallelepiped region R between the alignment jigs 7a and 7b including the leads 20.

Consequently, the leads 20 arranged as above are buried in the resin S. As this resin S, it is preferable to select a material having appropriate acoustic impedance and appropriate acoustic attenuation by which it functions as an acoustic damper. The resin S changes into the backing layer 1 by hardening.

Figure 22:
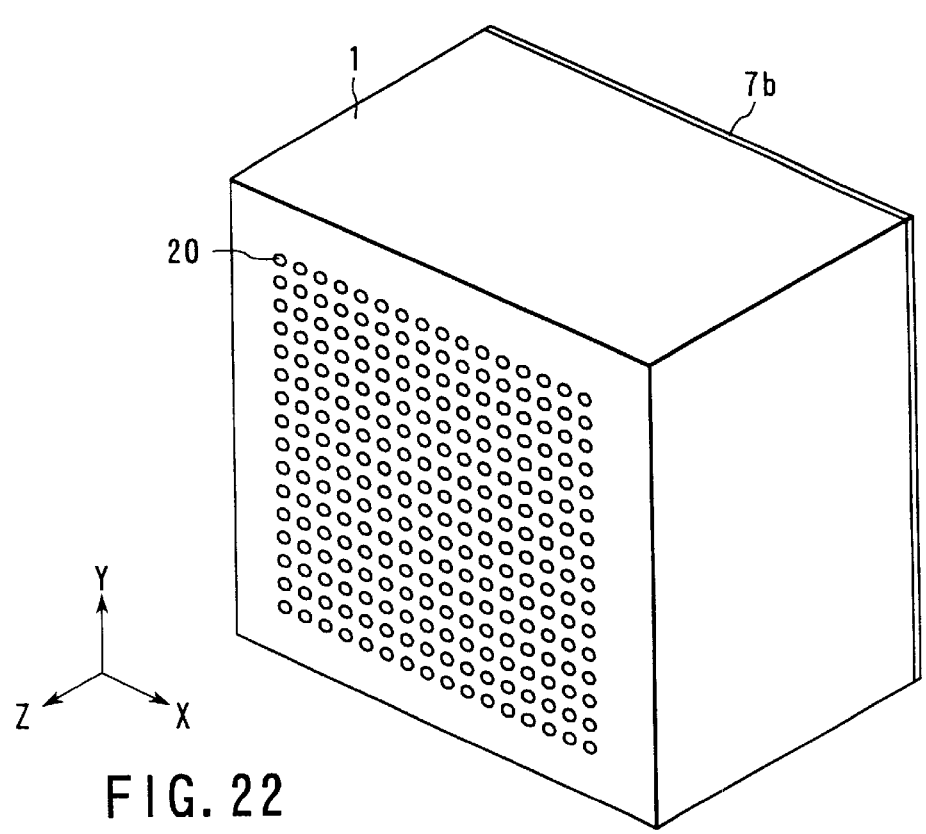
FIG. 22 is a view showing a step of removing the alignment jig on the front surface side from a backing layer in the method of manufacturing the ultrasonic transducer according to the second embodiment.

As shown in FIG. 22, the alignment jig 7a is removed from the surface of the backing layer 1 by using a technique such as mechanical processing or etching. After that, the surface of the backing layer 1 is flattened by cutting it together with the leads 20. This exposes the ends of the leads 20 to the surface of the backing layer 1. The alignment jig 7b on the back surface of the backing layer 1 can be either removed or left behind. When this backing layer 7b is removed, the back surface of the backing layer 1 need not be flattened by cutting. The rear ends of the leads 20 projecting from the lead holes 8 are used as electrical connecting terminals for external circuits.

As shown in FIGS. 23 and 24, a contact layer 11 as a thin metal film having a stacked structure of chromium and gold is formed on the flattened surface of the backing layer 1 by a technique such as vapor deposition or sputtering. This contact layer 11 is divided crosswise by grooves 12 to form contacts 11' for increasing the electrical contact area between the end portions of the leads 20 and discrete electrodes of the transducer elements 3. Since the contacts 11' are very thin, they do not deteriorate the acoustic characteristics.

After that, following the same procedure as in the first embodiment, the transducer elements 3 are formed in a matrix on the contacts 11' on the surface of the backing layer 1.

As described above, this embodiment can achieve an effect similar to that of the first embodiment, e.g., the bar-like leads 20 can be arranged in accordance with the arrangement of the transducer elements 3 by using the pair of alignment jigs 7a and 7b.

This second embodiment employs the leads 20 whose central portions are covered with an insulating material. However, coaxial wires manufactured by forming conductive layers on the coatings of the leads 20 can also be used. Since the leads 20 are shielded by the outer conductive layers, crosstalk between these leads can be reduced.

Third Embodiment

The third embodiment of the present invention will be described below. In the explanation of this third embodiment, the same reference numerals as in the first and second embodiments denote the same parts, and a detailed description thereof will be omitted.

Figure 25:
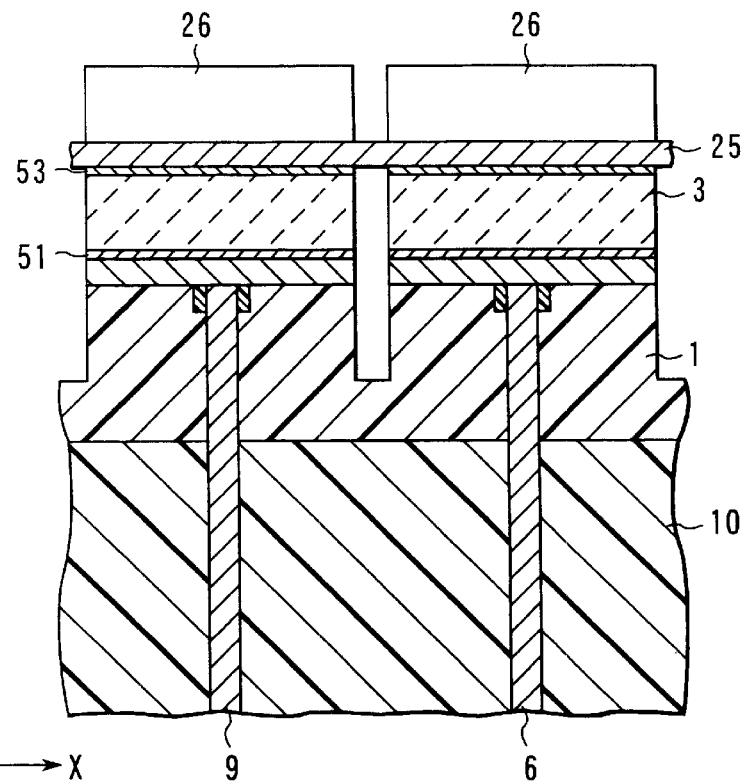
FIG. 25 is a sectional view of one transducer element of an ultrasonic transducer according to the third embodiment of the present invention.

As shown in FIG. 25, transducer elements 3 are arrayed on the surface of a backing layer 1 in which printed boards 10 are buried. Common electrodes 53 of the transducer elements 3 are connected together to a conductive layer 25 for grounding. Acoustic matching layers 26 are mounted on the transducer elements 3 via the conductive layer 25. In the backing layer 1, the printed boards 10 of the first embodiment or leads 20 of the second embodiment are buried.

Steps of manufacturing an ultrasonic transducer will be described below. In this embodiment, the steps up to the formation of the backing layer 1 are the same as in the first and second embodiments described above, so a detailed description of these steps will be omitted.

Figure 26:
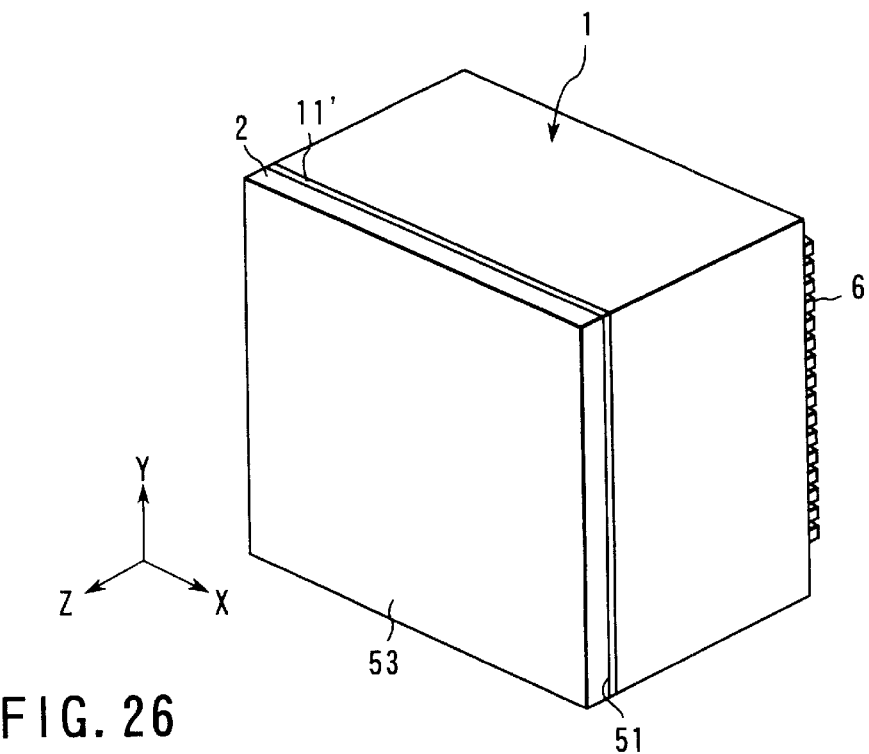
FIG. 26 is a perspective view showing a step of adhering a piezoelectric plate to the surface of a thin metal plate in a method of manufacturing the ultrasonic transducer according to the third embodiment.
Figure 27:
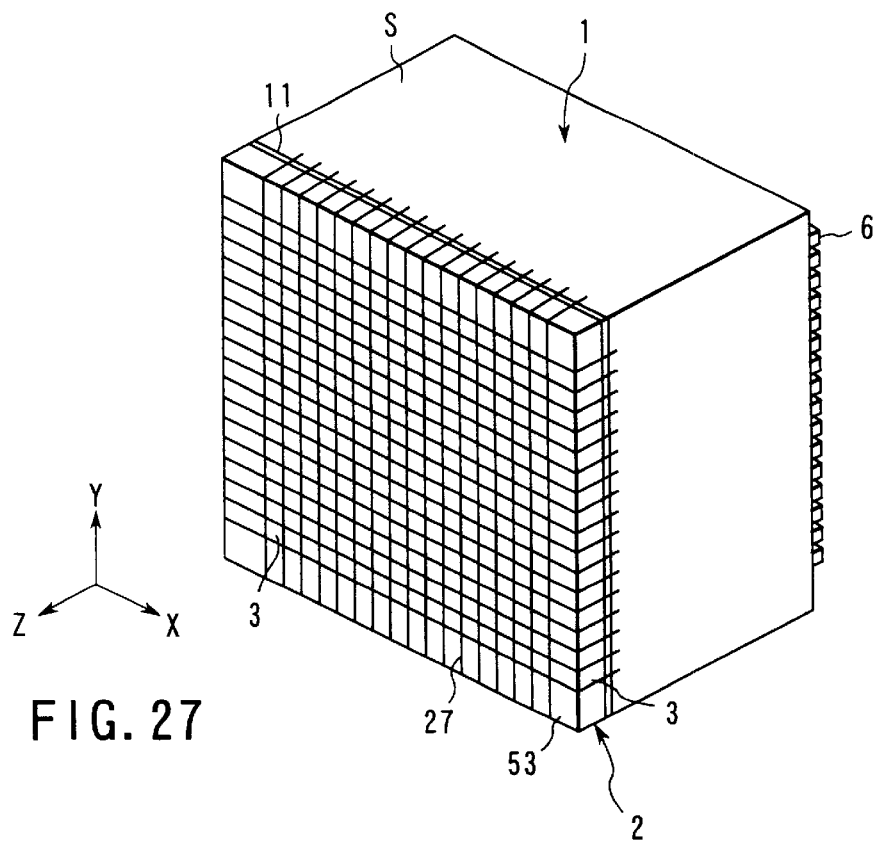
FIG. 27 is a perspective view showing a step of separating the piezoelectric plate in the method of manufacturing the ultrasonic transducer according to the third embodiment.

First, as shown in FIG. 26, a piezoelectric plate 2 such as piezoelectric ceramics is adhered on contacts 11' of the backing layer 1. The common electrodes 53 are formed on the surface of this piezoelectric plate 2, and discrete electrodes 51 are formed on the back surface. Next, as shown in FIG. 27, grooves 27 are formed crosswise to extend from the surface of the piezoelectric plate 2 to the outermost portion of the backing layer 1. With these grooves 27, the piezoelectric plate 2 is divided, forming a plurality of transducer elements 3 in a matrix.

Figure 28:
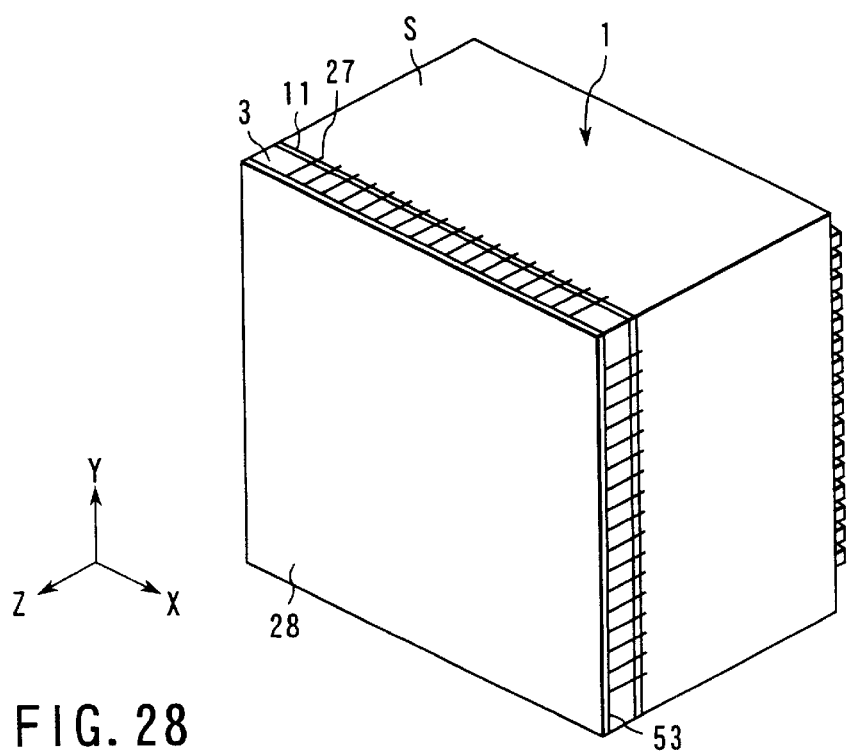
FIG. 28 is a perspective view showing a step of forming a conductive film on the surface of the piezoelectric plate in the method of manufacturing the ultrasonic transducer according to the third embodiment.

As shown in FIG. 28, a conductive film 28 formed by stacking a thin metal film and a resin is adhered to the surfaces of the common electrodes 53 of the transducer elements 3 by a conductive adhesive. This conductive film 28 is, e.g., a film formed by laminating a copper foil on the surface of a polyimide film, a film formed by laminating a metal foil on the two surfaces of a resin film, or a metal foil.

Figure 29:
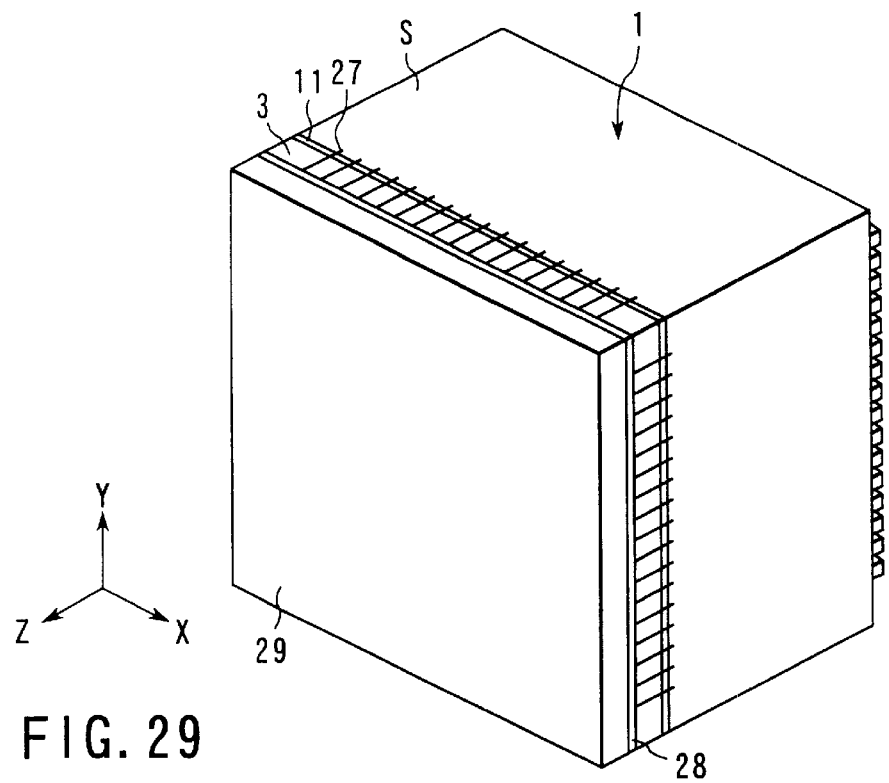
FIG. 29 is a perspective view showing a step of forming a resin layer for acoustic matching on the surface of the resin film in the method of manufacturing the ultrasonic transducer according to the third embodiment.
Figure 30:
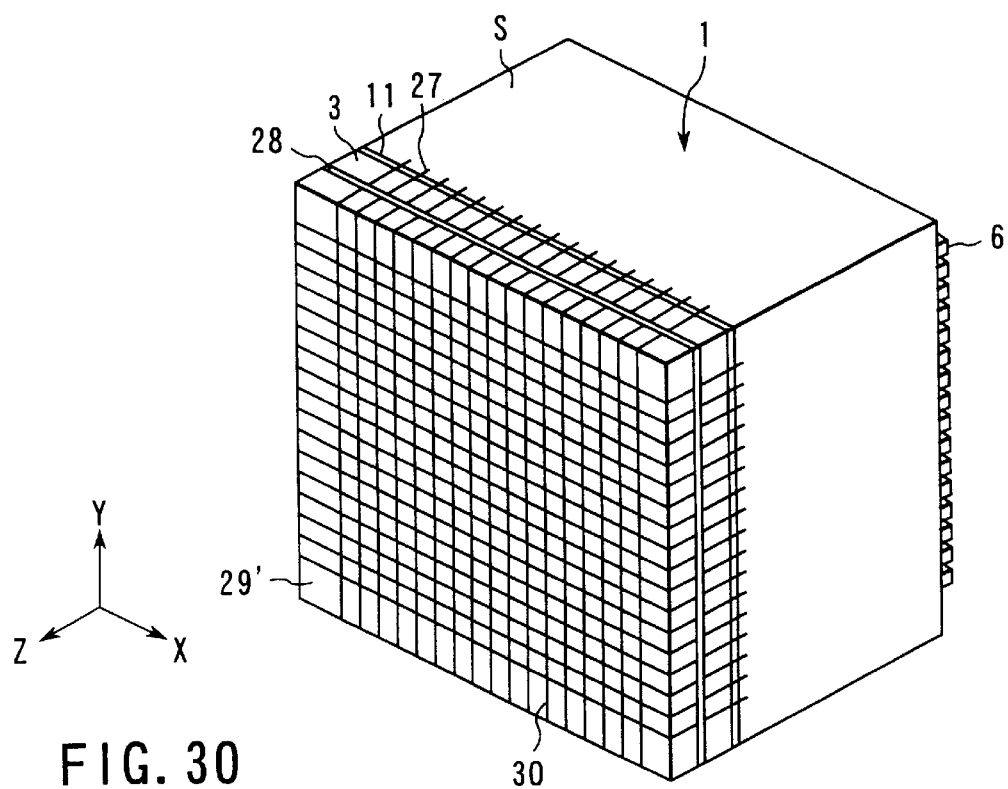
FIG. 30 is a perspective view showing a step of dividing the acoustic matching resin layer in the method of manufacturing the ultrasonic transducer according to the third embodiment.

As shown in FIGS. 29 and 30, an epoxy resin layer 29 is formed on the surface of the conductive film 28 so as to have a thickness suited to the acoustic matching characteristics. This epoxy resin layer 29 is divided crosswise with grooves 30 not to reach the conductive film 28 by using a dicing machine or a laser, thereby forming acoustic matching layers 29'. The material of the acoustic matching layers 29' is not restricted to an epoxy resin but can be some other type of resin. Also, each acoustic matching layer 29' need not be a single layer but can have a multilayered structure.

Note that the type of laser is selected and the intensity of the laser is adjusted so that the conductive film 28 is not divided and only the epoxy resin layer 29 on this conductive film 28 is selectively divided.

The intensity of the laser is adjusted so that a conductive layer (metal layer) is divided and a resin layer is not divided in the case conductive film 28 has a conductive layer and a resin layer.

Through the above steps, the ultrasonic transducer shown in FIG. 25 is manufactured. This embodiment can achieve an effect similar to those of the first and second embodiments. In addition, the conductive film 28 below the acoustic matching layers 29' is not divided but connected to the common electrodes 53 of the transducer elements 3. Therefore, no conductivity need be given to the acoustic matching layers, unlike in the first and second embodiments. This extends the range of selecting the material of the acoustic matching layers and facilitates the use of a multilayered structure. Consequently, optimum acoustic matching characteristics can be easily attained.

In the above embodiment, the acoustic matching layers 26 are formed by forming the epoxy resin layer 29 on the conductive film 28 and dividing this epoxy resin layer 29. However, the present invention is not limited to this arrangement. That is, a resin layer laminated on a metal foil, which is a material having superior acoustic characteristics and has a predetermined thickness, can also be used as the conductive film 28, without forming the epoxy resin layer 29. In this case, the acoustic matching layers 26 are formed by forming grooves, reaching the metal foil, in the resin layer formed on the metal foil.

Fourth Embodiment

The fourth embodiment of the present invention will be described below. In the explanation of this fourth embodiment, the same reference numerals as in the first, second, and third embodiments described above denote the same parts, and a detailed description thereof will be omitted.

Figure 31:
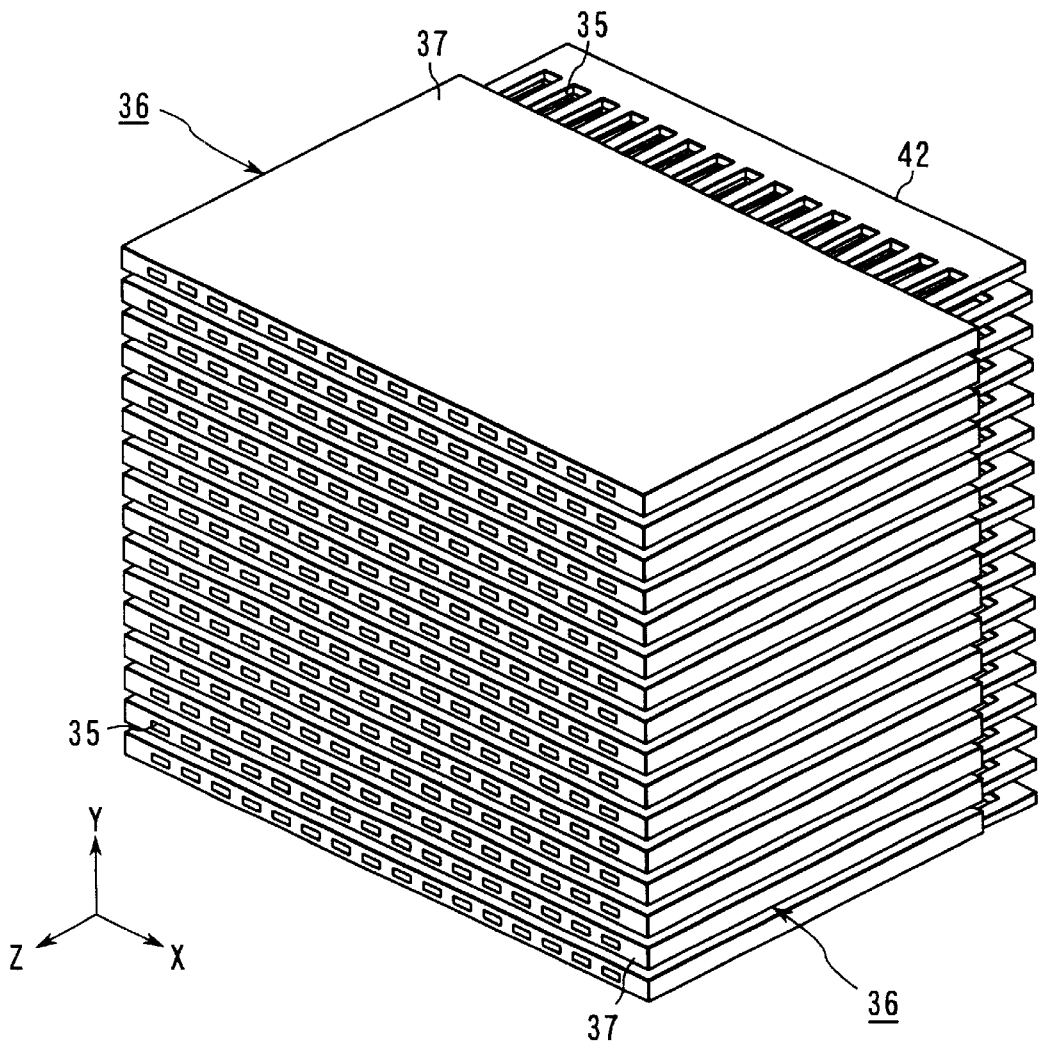
FIG. 31 is a perspective view showing a step of stacking flexible printed boards having connected leads in the method of manufacturing the ultrasonic transducer according to the third embodiment.
Figure 32:
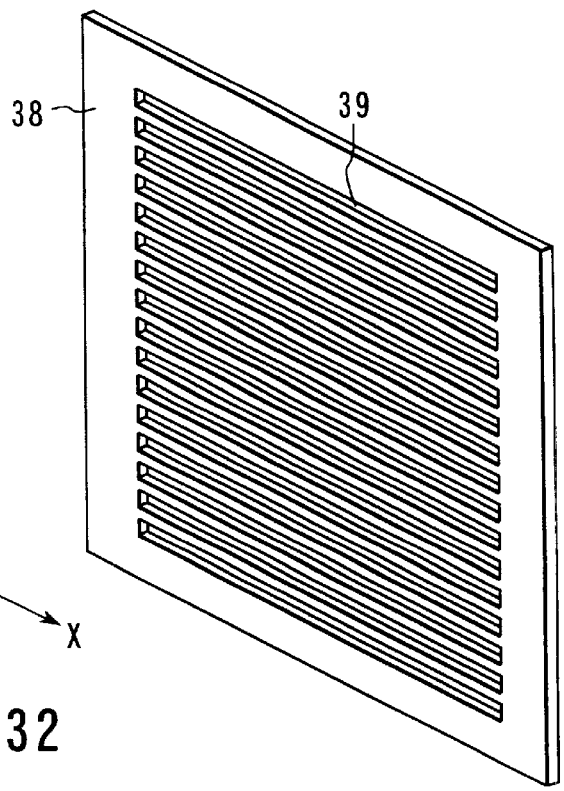
FIG. 32 is a perspective view showing an alignment jig used in a method of manufacturing an ultrasonic transducer according to the fourth embodiment.

In this embodiment, as shown in FIG. 31, leads 35 are connected in an end portion 42 projecting from a printed board 36 of an insulating material 37. A plurality of such printed boards 36 are overlapped. The connecting portions 42 are inserted into lead slits 39 of an alignment jig 38 as shown in FIG. 32, and gaps are fixed with an insulating resin. The lead slits 39 are formed parallel at the same pitch as the Y-direction pitch of transducer elements 3 in the alignment jig 38.

The alignment jig need not be a single member, but may have a multilayered structure made of workable materials such as a ceramic, metal, and resin. The lead slit formed in the alignment jig need not be a through hole slit extending through the alignment jig, but may be a blind groove formed midway along the thickness of the alignment jig.

In this embodiment, the leads 35 of one printed board 36 are inserted into on lead slit 39. However, the leads 35 of a plurality of printed boards 36 can also be inserted into one lead slit 39. Furthermore, in this embodiment one line of leads 35 are formed in one printed board 36. However, a plurality of lines of leads 35 can also be formed in one printed board 36. If this is the case, a plurality of lines of leads 35 of one printed board 36 are inserted into a plurality of adjacent lead slits 39.

Figure 33:
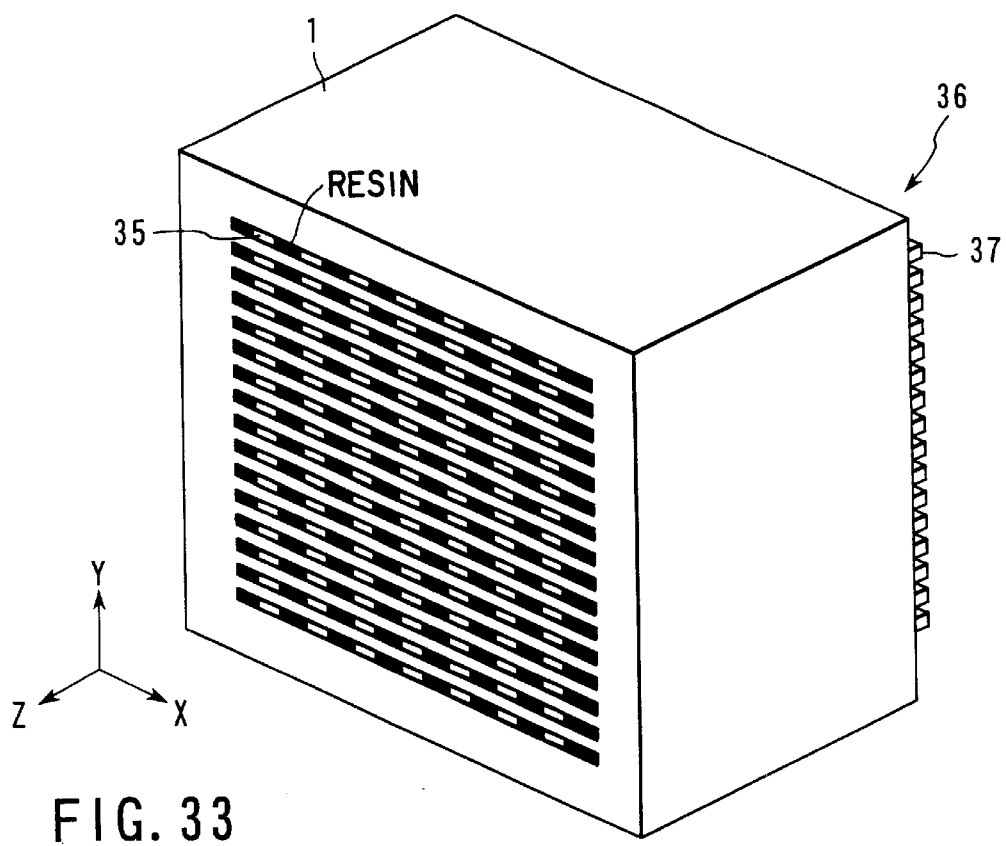
FIG. 33 is a perspective view showing a step of removing the alignment jig from a backing layer and flattening the surface of the backing layer in the method of manufacturing the ultrasonic transducer according to the fourth embodiment.

Next, as shown in FIG. 33, a backing layer 1 is formed on the back surface of the alignment jig 38. The printed boards 36 are buried in this backing layer 1. The alignment jig 38 is removed from the surface of the backing layer 1 by a technique such as mechanical processing or etching. After that, the surface of the backing layer 1 is flattened by cutting it together with the connecting portions 42 of the leads 35. The isolated end portions of the leads 35 are exposed to the cut surface of the backing layer 1. The alignment jig 38 does not deteriorate the acoustic characteristics because it is removed.

Instead of removing the alignment jig, the alignment jig may be cut thin to leave the thin alignment jig. In this case, the thickness of the thin alignment jig is adjusted to an odd number multiple of $\lambda/4$ where $\lambda$ is the wavelength of the center frequency of an ultrasonic wave generated by the transducer element. The ultrasonic wave generated by the transducer element is not reflected by the alignment jig but passes through the alignment jig. The ultrasonic wave then reaches the backing layer. The thin alignment jig does not deteriorate the acoustic characteristics.

Finally, as in the first embodiment, the transducer elements 3 are arrayed on the surface of this backing layer 1, thereby completing an ultrasonic transducer.

In this embodiment, the connected leads are isolated in the step of cutting the alignment jig thin. However, the leads can be isolated by forming grooves deep enough to divide the connected leads in the step of dividing the piezoelectric plate by vertical and horizontal grooves.

This embodiment can achieve an effect similar to those of the above embodiments. Additionally, the connecting portions of the leads are inserted into the lead slits of the alignment jig. This by far improves the workability compared to the aforementioned embodiments in which isolated leads are individually inserted into isolated holes.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing an ultrasonic transducer, comprising the steps of:
   inserting a plurality of bar-like leads into a plurality of lead holes or lead slits of a pair of alignment jigs, said plurality of lead holes or lead slits being formed in each of said alignment jigs;
   forming a backing layer by resin molding between said pair of alignment jigs, said plurality of leads being buried in said backing layer;
   removing at least one of said pair of alignment jigs from said backing layer and flattening a surface of said backing layer, the end portions of said leads being exposed to the flattened surface of said backing layer; and
   forming a transducer element array on the surface of said backing layer, said transducer element array comprising a plurality of transducer elements arrayed in a matrix, and discrete electrodes being formed on back surfaces of said transducer elements and electrically connected to the end portions of said leads.

2. A method according to claim 1, further comprising the step of filling gaps in said lead holes or lead slits with a conductive resin after said leads are inserted into said lead holes or lead slits.

3. A method according to claim 1, further comprising the step of forming a thin metal film on the flattened surface of said backing layer after said alignment jig is removed and the surface of said backing layer is flattened.

4. A method according to claim 3, further comprising the step of dividing said thin metal film in accordance with said plurality of leads after said thin metal film is formed.

5. A method according to claim 1, wherein the step of forming said transducer element array on the surface of said backing layer comprises the substeps of:
   attaching a piezoelectric plate to the surface of said backing layer, electrode layers being formed on front and back surfaces of said piezoelectric plate;
   forming an acoustic matching layer on the front surface of said piezoelectric plate; and
   forming grooves crosswise which extend from a surface of said acoustic matching layer to an outermost portion of said backing layer.

6. A method according to claim 5, wherein said acoustic matching layer has conductivity.

7. A method according to claim 5, wherein the step of forming said transducer element array on the surface of said backing layer further comprises the substep of forming a grounding electrode on the surfaces of said divided acoustic matching layers.

8. A method according to claim 7 wherein said grounding electrode comprises a metal layer and a resin layer.

9. A method according to claim 7, wherein said grounding electrode is comprised of a metal foil.

10. A method according to claim 1, wherein electronic circuits are formed together with said leads on said printed boards.

11. A method according to claim 1, wherein said alignment jig has said lead holes arranged in a matrix, and said leads are fitted in said lead holes or lead slits, respectively.

12. A method according to claim 1, wherein said alignment jig has said lead holes or lead slits arranged parallel to each other, and a plurality of leads are fitted in one of said lead holes or lead slits.

13. A method according to claim 1, wherein said lead hole or lead slit of said alignment jig is a blind hole or slits.

14. A method according to claim 1, wherein said alignment jig has a multilayered structure made of a plurality of different materials.

15. A method of manufacturing an ultrasonic transducer, comprising the steps of:

inserting a plurality of bar-like leads in a plurality of lead holes or lead slits or lead slits of a pair of alignment jigs, each of said pair of alignment jigs having said plurality of lead holes or lead slits or lead slits;

forming a backing layer between said pair of alignment jigs by resin molding, said plurality of leads being buried in said backing layer;

cutting at least one of said pair of alignment jigs from said backing layer, distal end portions of said leads being exposed from a surface of said cut alignment jig; and forming a transducer element array on the surface of said cut alignment jig, said transducer element array having a plurality of transducer elements arranged in a matrix, said transducer elements having back surfaces on which discrete electrodes are formed, and said discrete electrodes being electrically connected to said distal end portions of said leads.

16. A method according to claim 15, wherein the step of forming a transducer element array on the surface of said backing layer comprises the substeps of:

mounting a piezoelectric plate on the surface of said backing layer, said piezoelectric plate having front and back surfaces on which electrode layers are respectively formed;

forming vertical and horizontal grooves deep enough to reach a surface layer portion of said backing layer from the surface of said piezoelectric plate in order to divide the piezoelectric plate;

forming a grounding electrode on the surface of said divided piezoelectric plate; and forming an acoustic matching layer on a surface of said grounding electrode.

17. A method according to claim 16, wherein said grounding electrode comprises a metal layer and a resin layer.

18. A method according to claim 16, wherein said grounding layer is comprised of a metal foil.

* * * * *